(12) United States Patent
Takeda et al.

(10) Patent No.: US 9,851,293 B2
(45) Date of Patent: Dec. 26, 2017

(54) CONCENTRATION CALCULATION SYSTEM OF OPTICALLY ACTIVE SUBSTANCE, MANUFACTURING METHOD OF CONCENTRATION CALCULATION SYSTEM OF OPTICALLY ACTIVE SUBSTANCE, AND COMPUTER READABLE MEDIUM

(71) Applicant: FUJI XEROX CO., LTD., Tokyo (JP)

(72) Inventors: Kazutaka Takeda, Ebina (JP); Kazuyuki Matsushita, Ebina (JP); Kohei Yukawa, Ebina (JP); Hideaki Ozawa, Ebina (JP); Taku Kinoshita, Ebina (JP); Hideo Nakayama, Ebina (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 15/138,646

(22) Filed: Apr. 26, 2016

(65) Prior Publication Data
US 2016/0238518 A1 Aug. 18, 2016

Related U.S. Application Data

(63) Continuation of application No. PCT/JP2015/058350, filed on Mar. 19, 2015.

(30) Foreign Application Priority Data

Mar. 20, 2014 (JP) .................. 2014-059221
Mar. 9, 2015 (JP) .................. 2015-046453

(51) Int. Cl.
*G01N 21/21* (2006.01)
*G01N 21/31* (2006.01)
*G01N 33/49* (2006.01)

(52) U.S. Cl.
CPC ............. *G01N 21/21* (2013.01); *G01N 21/31* (2013.01); *G01N 33/492* (2013.01); *G01N 2021/3129* (2013.01)

(58) Field of Classification Search
CPC ........ G01N 21/21; G01N 21/25; G01N 21/27; G01N 21/31; G01N 21/314;
(Continued)

(56) References Cited

U.S. PATENT DOCUMENTS 3,481,671 A * 12/1969 West ...................... G01N 21/21
356/327
5,788,632 A * 8/1998 Pezzaniti ............... G01N 21/21
356/368

(Continued)

FOREIGN PATENT DOCUMENTS

JP   H09-138231 A    5/1997
JP   2002-082046 A   3/2002

(Continued)

OTHER PUBLICATIONS

Jun. 2, 2015 International Search Report issued in International Patent Application No. PCT/JP2015/058350.

(Continued)

*Primary Examiner* — Gordon J Stock, Jr.
(74) *Attorney, Agent, or Firm* — Oliff PLC

(57) ABSTRACT

A concentration calculation system calculates a concentration of the optically active substance based on a formula. The formula includes a first function representing wavelength dependence of an optical rotation of a first optically-active substance, and a second function representing wavelength dependence of an optical rotation of a second optically-active substance. In the first function, concentration of the first optically-active substance has an unknown value, and an inherent value for defining a characteristic of
(Continued)

optical rotatory dispersion of the first optically-active substance is a known value or an unknown value within a certain limited range. In the second function, an inherent value for defining a characteristic of optical rotatory dispersion of the second optically-active substance is an unknown value. The concentration of the first optically-active substance is calculated based on the formula and optical rotations of measurement target respectively corresponding to a plurality of wavelengths, by using a least-squares method.

9 Claims, 19 Drawing Sheets

(58) Field of Classification Search
CPC .......... G01N 21/3151; G01N 21/3577; G01N 21/59; G01N 21/5907; G01N 33/492; G01N 2201/0683; G01N 2021/3129; G01N 2021/3133; G01N 2021/3148; G01N 2021/3185; G01N 2021/5969
See application file for complete search history.

(56) References Cited

U.S. PATENT DOCUMENTS

| | | | | |
|---|---|---|---|---|
| 5,822,067 A * | 10/1998 | Yanik | ............. | G01N 21/21 356/368 |
| 6,166,807 A * | 12/2000 | Kawamura | ............... | G01J 4/00 356/364 |
| 6,327,037 B1 * | 12/2001 | Chou | .................. | G01J 4/04 356/484 |
| 6,620,622 B1 * | 9/2003 | Kawamura | ............ | G01N 21/21 250/225 |
| 6,885,882 B2 * | 4/2005 | Cote | .................. | A61B 5/14558 600/319 |
| 2005/0154269 A1 | 7/2005 | Cameron | | |
| 2008/0117420 A1 * | 5/2008 | Scarpaci | ................ | G01N 21/21 356/364 |
| 2014/0039282 A1 | 2/2014 | Goto et al. | | |
| 2017/0020385 A1 * | 1/2017 | Matsushita | .......... | A61B 3/0008 |

FOREIGN PATENT DOCUMENTS

| | | |
|---|---|---|
| JP | 2007-518990 A | 7/2007 |
| JP | 2008-209204 A | 9/2008 |
| JP | 2012-112907 A | 6/2012 |
| JP | 2014-032146 A | 2/2014 |

OTHER PUBLICATIONS

Jun. 2, 2015 Written Opinion issued in International Patent Application No. PCT/JP2015/058350.

* cited by examiner

FIG. 7A
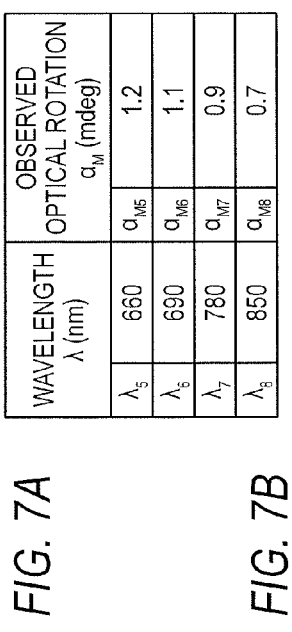
FIG. 7B
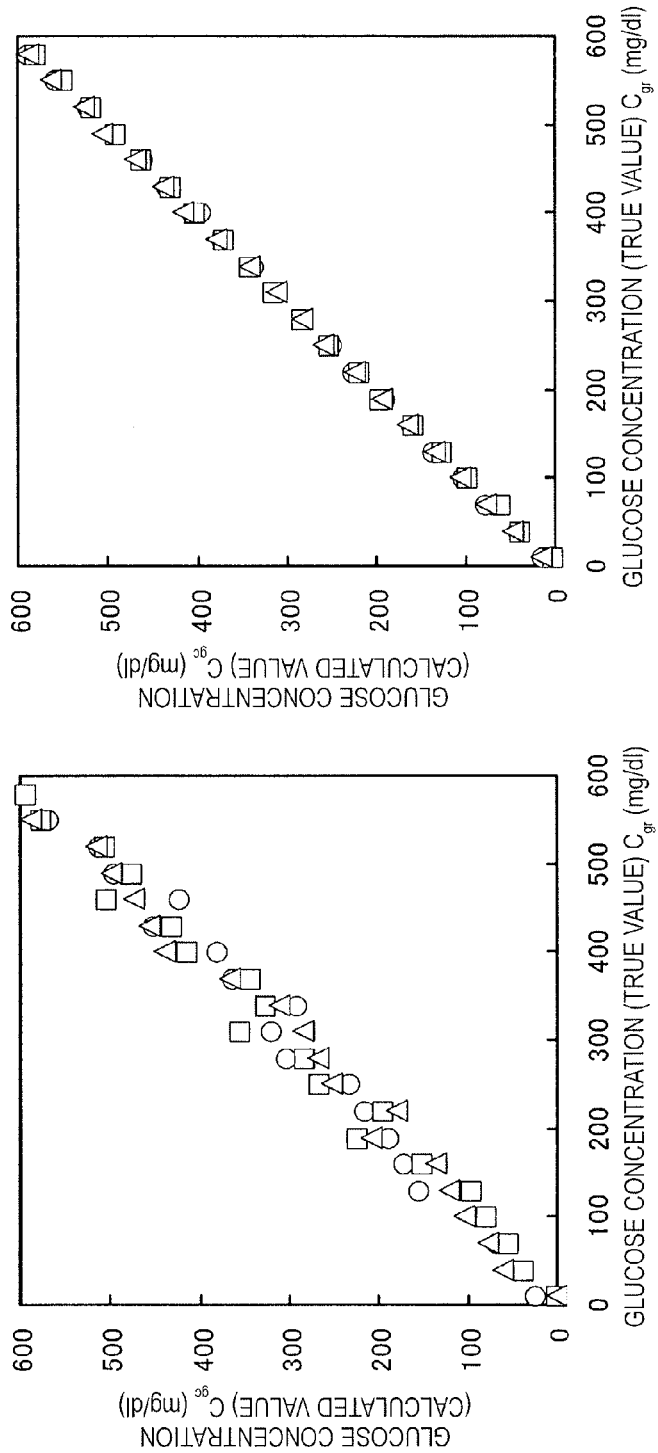
FIG. 7C
FIG. 7D

FIG. 9
(a) NO RESTRICTION CONDITION
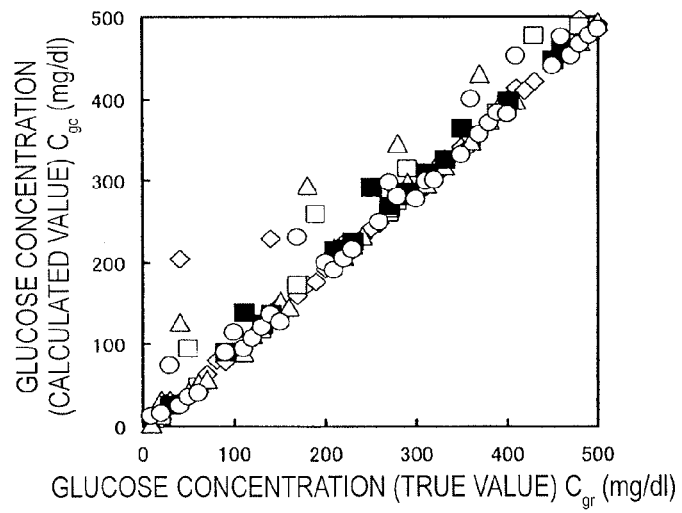
(b) $C_{gc} > 0, A_x < 0,$
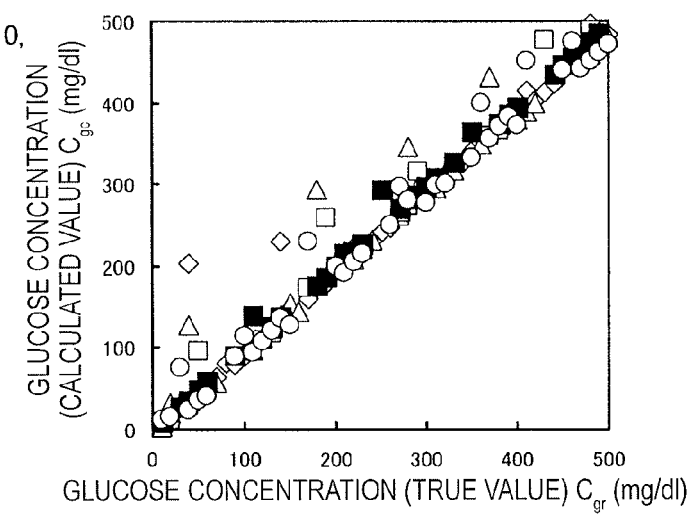
(c) $C_{gc} > 0, A_x < 0,$
$250 \leqq \lambda_x \leqq 300$
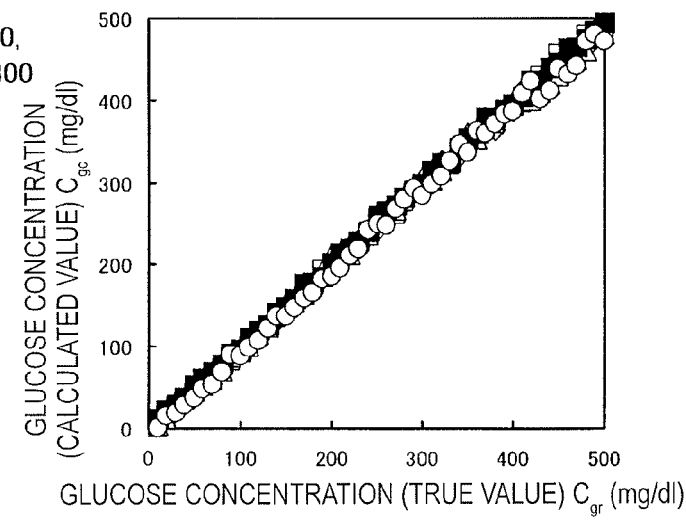

FIG. 10
(a) $C_{gc}$ INITIAL VALUE: 100
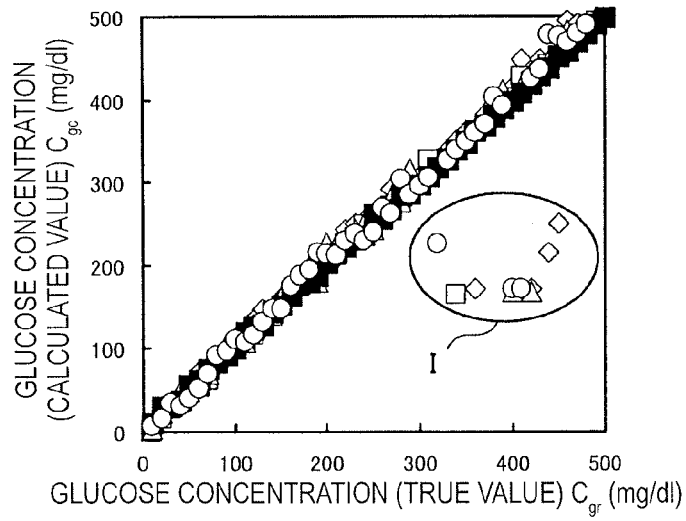
(b) $C_{gc}$ INITIAL VALUE: 300
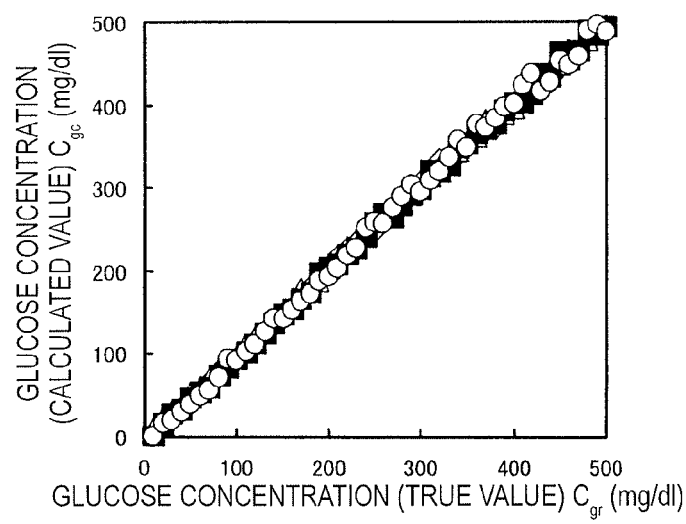
(c) $C_{gc}$ INITIAL VALUE: 500
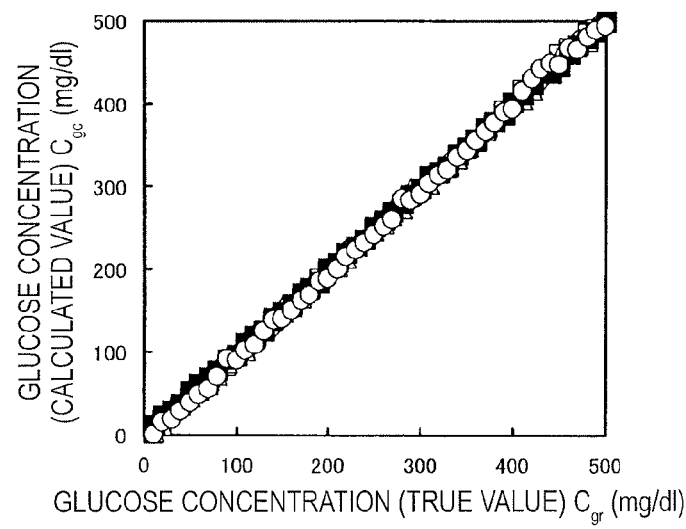

FIG. 11
(a) RESTRICTION CONDITION A
$C_{gc} > 0, A_x < 0,$
$200 \leq \lambda_x \leq 300$
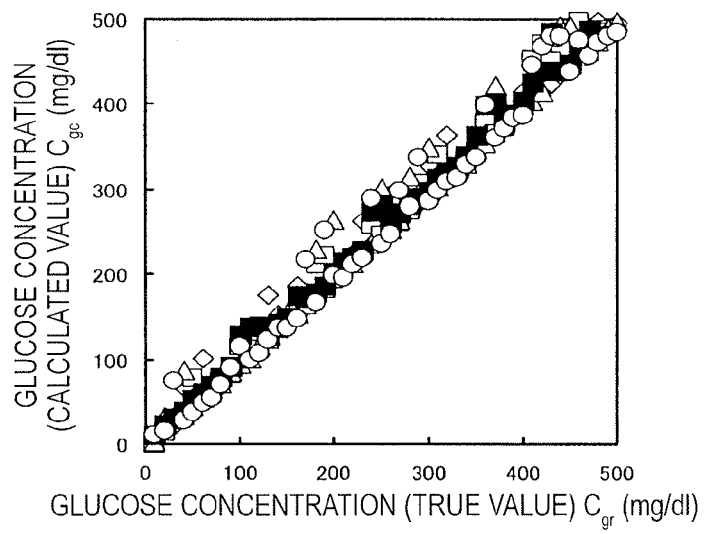
(b) RESTRICTION CONDITION B
$C_{gc} > 0, A_x < 0,$
$250 \leq \lambda_x \leq 300$
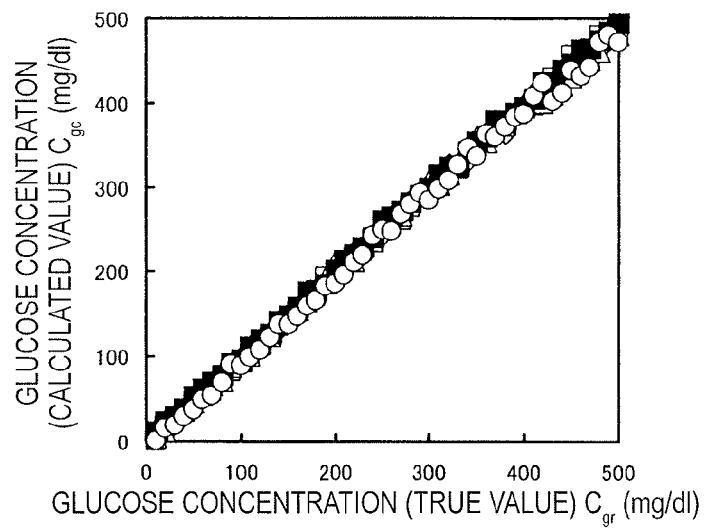
(c)
| RESTRICTION CONDITION | VALUE OF OBJECTIVE FUNCTION | CONCENTRATION $C_{gc}$ (mg/dl) |
|---|---|---|
| A | $3.5 \times 10^{-3}$ | 230 |
| B | $1.56 \times 10^{-5}$ | 198 |

FIG. 15A

| # | FIRST OPTICALLY-ACTIVE SUBSTANCE | SECOND OPTICALLY-ACTIVE SUBSTANCE | FORMULA |
|---|---|---|---|
| 1 | GLUCOSE | OTHER SUBSTANCE INCLUDED IN AQUEOUS HUMOR | FORMULA (11) |
| 2 | ALBUMIN | OTHER SUBSTANCE INCLUDED IN AQUEOUS HUMOR | FORMULA (12) |
| 3 | GLUCOSE ALBUMIN | OTHER SUBSTANCE INCLUDED IN AQUEOUS HUMOR | FORMULA (6) |
| 4 | GLUCOSE | ALBUMIN OTHER SUBSTANCE INCLUDED IN AQUEOUS HUMOR | FORMULA (6) |
| 5 | GLUCOSE | ALBUMIN | FORMULA (10) |

FIG. 15B

| OPTICALLY ACTIVE SUBSTANCE | INHERENT VALUE | |
|---|---|---|
| GLUCOSE | $A_g$ | $1.72 \times 10^7$ |
| | $\lambda_g$ | 150 |
| ALBUMIN | $\lambda_a$ | 250 |

FIG. 18

| OPTICAL ROTATION $\alpha_{M1}$ AT WAVELENGTH $\lambda_1$ | OPTICAL ROTATION $\alpha_{M2}$ AT WAVELENGTH $\lambda_2$ | OPTICAL ROTATION $\alpha_{M3}$ AT WAVELENGTH $\lambda_3$ | CONCENTRATION $C_{gc}$ OF OPTICALLY ACTIVE SUBSTANCE (GLUCOSE) |
|---|---|---|---|
| $\alpha_1$ | $\alpha_1$ | $\alpha_1$ | $C_{g111}$ |
| $\alpha_2$ | $\alpha_1$ | $\alpha_1$ | $C_{g211}$ |
| $\alpha_3$ | $\alpha_1$ | $\alpha_1$ | $C_{g311}$ |
| ........ | ........ | ........ | ........ |
| $\alpha_n$ | $\alpha_n$ | $\alpha_n$ | $C_{gnnn}$ |

000# CONCENTRATION CALCULATION SYSTEM OF OPTICALLY ACTIVE SUBSTANCE, MANUFACTURING METHOD OF CONCENTRATION CALCULATION SYSTEM OF OPTICALLY ACTIVE SUBSTANCE, AND COMPUTER READABLE MEDIUM

CROSS REFERENCE TO RELATED APPLICATION

This is a continuation of International Application No. PCT/JP2015/058350 filed on Mar. 19, 2015, and claims priorities from Japanese Patent Application No. 2014-059221, filed on Mar. 20, 2014 and Japanese Patent Application No. 2015-046453, filed on Mar. 9, 2015.

BACKGROUND

Technical Field

The present invention relates to a concentration calculation system of an optically active substance, a manufacturing method of the concentration calculation system of the optically active substance, and a computer readable medium.

SUMMARY

According to an aspect of the present invention, there is provided a concentration calculation system of an optically active substance, that calculates a concentration of the optically active substance based on a formula representing an optical rotation, the formula including a first function representing wavelength dependence of an optical rotation of at least one first optically-active substance, and a second function representing wavelength dependence of an optical rotation of at least one second optically-active substance. In the first function, concentration of the first optically-active substance has an unknown value, and at least one inherent value for defining a characteristic of optical rotatory dispersion of the first optically-active substance is a known value or an unknown value within a certain limited range. In the second function, at least one inherent value for defining a characteristic of optical rotatory dispersion of the second optically-active substance is an unknown value. The concentration of the first optically-active substance is calculated based on the formula and optical rotations of measurement target respectively corresponding to a plurality of wavelengths, by using a least-squares method.

BRIEF DESCRIPTION OF DRAWINGS

Exemplary embodiment(s) of the present invention will be described in detail based on the following figures, wherein:

FIG. 7A is a diagram illustrating a case where the glucose concentration $C_g$ is obtained from the observed optical rotation $\alpha_M$ by using the formula (10) and by using a wavelength λ of a wavelength region different from that in a short wavelength region of 410 nm to 470 nm in FIGS. 6A and 6B and illustrates a relationship between a wavelength λ in a long wavelength region of 660 nm to 850 nm, and the observed optical rotation $\alpha_M$;

FIG. 7B illustrates a relationship between the glucose concentration (true value) $C_{gr}$ and the glucose concentration (calculated value) $C_{gc}$ in FIG. 7A;

FIG. 7C is a diagram illustrating a case where the glucose concentration $C_g$ is obtained from the observed optical rotation $\alpha_M$ by using the formula (10) and by using a wavelength λ of a wavelength region different from that in a short wavelength region of 410 nm to 470 nm in FIGS. 6A and 6B and illustrates a relationship between a wavelength λ in the short wavelength region and the long wavelength region, and the observed optical rotation $\alpha_M$;

FIG. 7D illustrates a relationship between the glucose concentration (true value) $C_{gr}$ and the glucose concentration (calculated value) $C_{gc}$ in FIG. 7C;

FIG. 9 is a diagram for a comparison between a case where a restriction condition for an unknown value is not provided, and a case where a restriction condition for an unknown value is provided when the glucose concentration (calculated value) $C_{gc}$ is calculated by using the formula (11), in which (a) illustrates the case where a restriction condition for an unknown value is not provided, and in which (b) and (c) illustrate the case where a restriction condition for an unknown value is provided;

FIG. 10 is a diagram for a comparison between initial values of the glucose concentration (calculated value) $C_{gc}$ set when the glucose concentration (calculated value) $C_{gc}$ is calculated by using the formula (11), in which (a) illustrates a case where the initial value is 100 ml/dl, in which (b) illustrates a case where the initial value is 300 ml/dl, and in which (c) illustrates a case where the initial value is 500 ml/dl;

FIG. 11 is a diagram illustrating an example in which a preferable calculated value is obtained from concentration C of an optically active substance, which is calculated under restriction conditions A and B, in which (a) illustrates a relationship between the glucose concentration (true value) $C_{gr}$ and the glucose concentration (calculated value) $C_{gc}$ in a case of the restriction condition A, in which (b) illustrates a relationship between the glucose concentration (true value) $C_{gr}$ and the glucose concentration (calculated value) $C_{gc}$ in a case of the restriction condition B, and in which (c) illustrates a relationship between the value of the objective function calculated for a measurement target having the certain glucose concentration $C_{gr}$ and the glucose concentration $C_{gc}$;

FIG. 15A is a diagram illustrating an example of a formula stored in a formula storage unit and an inherent value stored in an inherent value storage unit and illustrates an example of the formula (algorithm) stored by the formula storage unit;

FIG. 15B is a diagram illustrating an example of a formula stored in a formula storage unit and an inherent value stored in an inherent value storage unit and illustrates an example of the inherent values stored by the inherent value storage unit;

FIG. 18 is a diagram illustrating an example of an LUT stored in an LUT storage unit;

DETAILED DESCRIPTION

Hereinafter, an exemplary embodiment according to the present invention will be described with reference to the accompanying drawings.

(Concentration Calculation System 1 of an Optically Active Substance)

Figure 1:
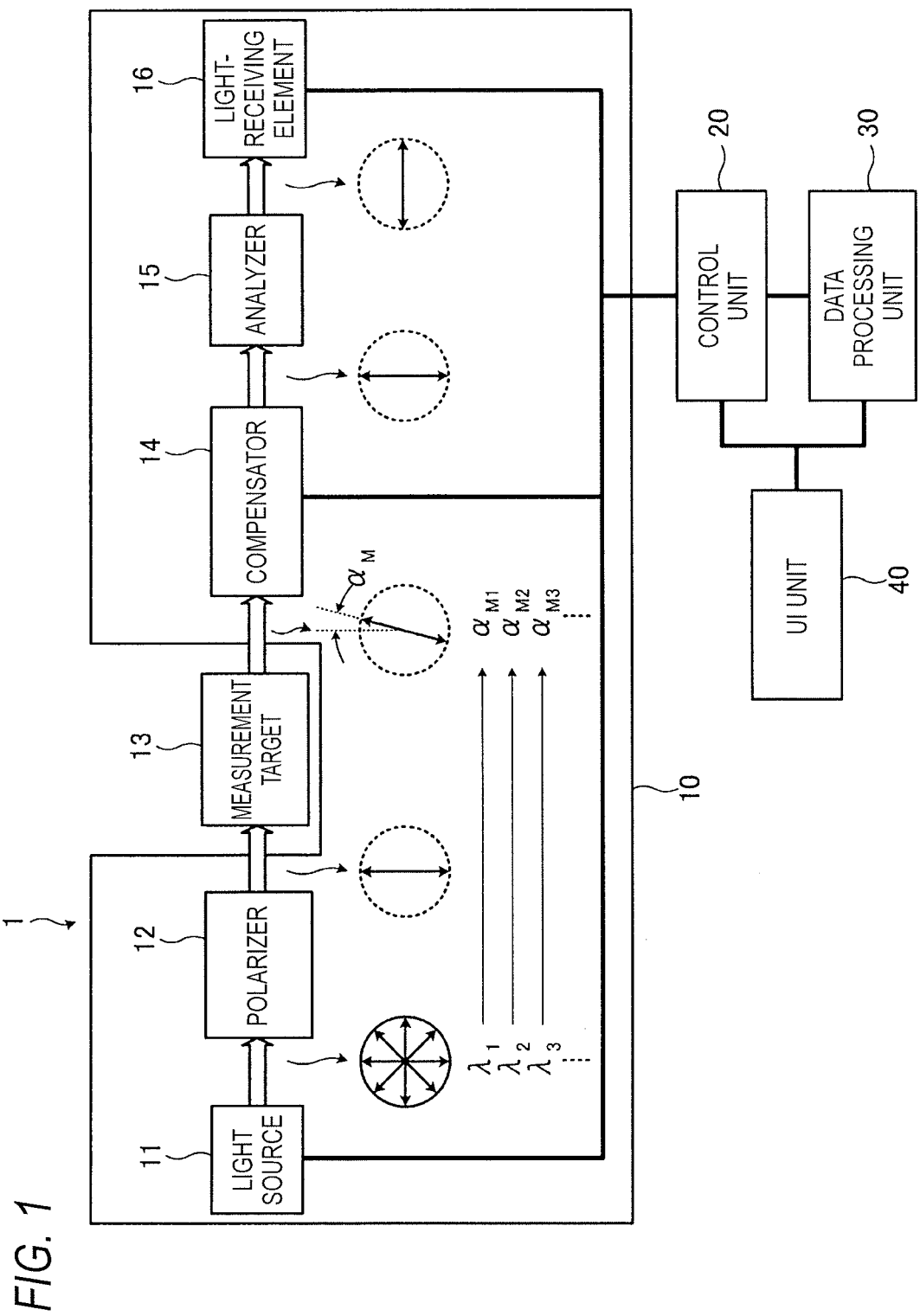
FIG. 1 is a diagram illustrating an example of a configuration of a concentration calculation system of an optically active substance, to which an exemplary embodiment is applied.

FIG. 1 is a diagram illustrating an example of a concentration calculation system 1 of an optically active substance, to which an embodiment is applied.

The optically active substance has optical activity which rotates a polarization plane of linear polarized light with which irradiation is performed. Here, in the embodiment, the polarization plane refers to a plane in which an electric field is vibrated regarding linear polarized light.

The concentration calculation system 1 of an optically active substance illustrated in FIG. 1 irradiates a measurement target 13, which includes an optically active substance, with linear polarized light, and calculates concentration of the optically active substance included in the measurement target 13 by measuring a rotated angle (observed optical rotation $\alpha_M$) of a polarization plane observed after the linear polarized light is transmitted through the measurement target 13.

Here, optical rotation observed a case where the measurement target 13 includes one optically active substance is represented as optical rotation $\alpha$, and optical rotation observed a case where the measurement target 13 includes a plurality of optically active substances is represented as optical rotation $\alpha_M$. As will be described later, the observed optical rotation $\alpha_M$ is set to be the sum of optical rotations $\alpha$ by the optically active substances included in the measurement target 13. Each of the optical rotations $\alpha$ of the optically active substances included in the measurement target 13 reflects concentration of the corresponding optically active substance included in the measurement target 13.

Even when the measurement target 13 includes a plurality of optically active substances, the concentration of an optically active substance wanted to be obtained may be known.

The concentration of the active substance wanted to be obtained refers to concentration of an optically active substance which is wanted to be known by a user in a case where the measurement target 13 includes a plurality of optically active substances. The concentration of the active substance wanted to be obtained also refers to concentration of an optically active substance which is a target of a display to an UI unit 40 (see FIG. 2), and the like. Such an optically active substance may be described as a first optically-active substance, and the remaining optically-active substance may be described as a second optically-active substance. A plurality of first optically-active substances may be provided. The second optically-active substance is an optically active substance other than the first optically-active substance. However, in a case where a plurality of optically active substances other than the first optically-active substance are provided, distinguishment between the plurality of optically active substances may be not required, and collection of some or all of the optically active substances other than the first optically-active substance may be set as the second optically-active substance.

The concentration calculation system 1 of an optically active substance includes a measuring unit 10, a control unit 20, a data processing unit 30, and the UI unit 40. The measuring unit 10 is connected to the control unit 20. The control unit 20 is connected to the data processing unit 30. The UI unit 40 is connected to the control unit 20 and the data processing unit 30. The connection may be wired or wireless.

The measuring unit 10 irradiates the measurement target 13, which includes an optically active substance, with linear polarized light, and measures a rotated angle (observed optical rotation $\alpha_M$) of a polarization plane observed after the linear polarized light is transmitted through the measurement target 13.

The control unit 20 controls the measuring unit 10 to measure the observed optical rotation $\alpha_M$, and transmits measurement data to the data processing unit 30. The measurement data is obtained by combining a wavelength $\lambda$ used in the measurement, and the observed optical rotation $\alpha_M$.

The data processing unit 30 calculates concentration of the optically active substance included in the measurement target 13 from the measurement data which is received from the control unit 20, and is a combination of the wavelength $\lambda$ and the observed optical rotation $\alpha_M$. The data processing unit 30 performs the calculation through numerical calculation processing and transmits the calculated concentration to the UI unit 40.

The UI unit 40 includes an input device and an output device. The input device receives an input of data or an instruction from a user, and includes a keyboard and the like. The output device displays a processing result and the like to the user, and includes a display and the like.

A user instructs the control unit 20 of an operation of the measuring unit 10 through the input device of the UI unit 40, such as a keyboard. The user inputs a formula or an inherent value which will be described later to the data processing unit 30.

The user obtains a state of an operation of the measuring unit 10 or concentration of an optically active substance wanted to be obtained from the data processing unit 30, through the output device of the UI unit 40, such as a display.

The measuring unit 10 includes a light source 11, a polarizer 12, a compensator 14, an analyzer 15, and a light-receiving element 16. The light source 11 emits light having a predetermined wavelength. The polarizer 12 extracts linear polarized light of a predetermined polarization plane, from the light emitted by the light source 11. The compensator 14 rotates the polarization plane of linear polarized light transmitted through the measurement target 13. The analyzer 15 causes linear polarized light of the predetermined polarization plane to be transmitted therethrough. The light-receiving element 16 receives light transmitted through the analyzer 15. These members constitute one optical system.

In the measuring unit 10 illustrated in FIG. 1, arrows in circles are respectively provided between the light source 11 and the polarizer 12, between the polarizer 12 and the measurement target 13, between the measurement target 13 and the compensator 14, between the compensator 14 and the analyzer 15, and between the analyzer 15 and the light-receiving element 16. Each of the arrows in circles indicates a form of polarization viewed from a traveling direction of the light.

Here, it is assumed that the measurement target 13 includes a plurality of optically active substances.

The light source 11 may be a light source such as a light-emitting diode (LED) or a lamp, which has a wide bandwidth. The light source 11 may be a light source such as a laser, which has a narrow bandwidth. As the light source 11, a light source which enables irradiation with light having at least two or more wavelengths is used. As the wavelength range of the light, for example, a wavelength range in a region in which the optical rotation $\alpha$ by an optically active substance included in the measurement target 13 can be approximate in the Drude monomial expression (which will be described later) is used. An example of the wavelength range is 400 nm to 900 nm.

Here, it is assumed that light emitted by the light source 11 includes light having a random polarization plane as illustrated in FIG. 1. The light emitted by the light source 11 may be linear polarized light. In this case, the polarizer 12 which will be described the next may be not required.

The polarizer 12 is, for example, a Nicol prism and the like. The polarizer 12 transmits the linear polarized light having a predetermined polarization plane, from light which is incident thereto and has a random polarization plane. In FIG. 1, as an example, it is assumed that linear polarized light of a polarization plane parallel to a surface of paper is transmitted.

Regarding the linear polarized light transmitted through the polarizer 12, the polarization plane thereof is rotated by an optically active substance included in the measurement target 13. In FIG. 1, it is assumed that the polarization plane is rotated as much as an angle $\alpha_M$ (observed optical rotation $\alpha_M$).

The compensator 14 is, for example, a magneto-optical element such as a Faraday element using garnet and the like. The compensator 14 rotates the polarization plane of linear polarized light by using a magnetic field.

The analyzer 15 transmits linear polarized light of a predetermined polarization plane, similar to the polarizer 12.

The light-receiving element 16 is a light-receiving element such as a silicon diode. The light-receiving element 16 outputs an output signal corresponding to intensity of light.

The measuring unit 10 described above is only an example, and may include other optical elements such as a mirror, a lens, a wavelength plate, and a prism.

Next, an example of a measuring method of the observed optical rotation $\alpha_M$, which is performed by the measuring unit 10 will be described.

Firstly, in a state where the measurement target 13 is not put (removed), the compensator 14 and the analyzer 15 in an optical system are set so as to cause an output signal of the light-receiving element 16 to be smallest. The optical system is configured from the light source 11, the polarizer 12, the compensator 14, the analyzer 15, and the light-receiving element 16. In the state where the measurement target 13 is not put, a polarization plane of linear polarized light transmitted through the polarizer 12 is perpendicular to a polarization plane of light transmitted through the analyzer 15.

In FIG. 1, the polarization plane of the polarizer 12 and the polarization plane before light is transmitted through the analyzer 15 are parallel to the surface of paper tighter. However, in a case where the polarization plane is rotated by the compensator 14, the polarization plane before light is transmitted through the analyzer 15 may be inclined from a surface parallel to the surface of paper. That is, in a case where the measurement target 13 is not put into the measuring unit 10, the compensator 14 and the analyzer 15 may be set so as to cause an output signal of the light-receiving element 16 to be smallest.

Then, the measurement target 13 is put into the measuring unit 10. The polarization plane is rotated by an optically active substance included in the measurement target 13. Thus, an output signal from the light-receiving element 16 is shifted from the minimum value. Accordingly, a magnetic field applied to the compensator 14 is set to cause the output signal from the light-receiving element 16 to be smallest. That is, the polarization plane is caused to be rotated by the compensator 14 and is caused to be perpendicular to the polarization plane of the light transmitted through the analyzer 15.

An angle of the polarization plane rotated by the compensator 14 corresponds to the observed optical rotation $\alpha_M$ occurring by the optically active substance included in the measurement target 13. A relationship between the size of the magnetic field applied to the compensator 14 and the angle of the rotated polarization plane has been known in advance. Thus, the observed optical rotation $\alpha_M$ is found from the size of the magnetic field applied to the compensator 14.

As a method of obtaining the observed optical rotation $\alpha_M$, an example using the compensator 14 is described. However, observed optical rotation $\alpha_M$ may be obtained by using a member other than the compensator 14. FIG. 1 illustrates an orthogonal polarizer method (using a compensator) which is the most basic measuring method for measuring a rotated angle (optical rotation). However, other measuring methods such as a rotating-analyzer method or a Faraday modulation method, and an optical delay modulation method may be applied.

The measurement target 13 is irradiated with light having a plurality of wavelengths $\lambda_1, \lambda_2, \lambda_3, \ldots$, from the light source 11, and each of observed optical rotations $\alpha_{M1}, \alpha_{M2}, \alpha_{M3}, \ldots$ for each of the plurality of wavelengths $\lambda_1, \lambda_2, \lambda_3, \ldots$, is obtained. In this manner, in a case where a plurality of wavelengths $\lambda$ and observed optical rotations $\alpha_M$ are provided, indication as the wavelengths $\lambda_1, \lambda_2, \lambda_3, \ldots$, and the observed optical rotations $\alpha_{M1}, \alpha_{M2}, \alpha_{M3}, \ldots$ is performed. Such indication is, similarly, applied to other cases.

The control unit 20 controls setting (switching) of the wavelengths $\lambda_1, \lambda_2, \lambda_3, \ldots$ of the light emitted by the light source 11, and controls On/Off. The control unit 20 sets the magnetic field applied to the compensator 14 so as to cause an output signal of the light-receiving element 16 to be smallest. The control unit 20 transmits measurement data $(\lambda_1:\alpha_{M1}, \lambda_2:\alpha_{M2}, \lambda_3:\alpha_{M3}, \ldots)$ to the data processing unit 30. The measurement data is a combination of the wavelength $\lambda$ and the observed optical rotation $\alpha_M$ measured by using the wavelength $\lambda$, by using the magnetic field applied to the compensator 14.

The data processing unit 30 calculates the concentration of an optically active substance included in the measurement target 13, based on the measurement data $(\lambda_1:\alpha_{M1}, \lambda_2:\alpha_{M2}, \lambda_3:\alpha_{M3}, \ldots)$ which is a combination of the wavelength $\lambda$ and the observed optical rotation $\alpha_M$.

Most of substances included in a living body are optically active substance having optical activity. Thus, a concentration measuring method of using optical activity of an optically active substance may be applied to measuring of concentration of an optically active substance included in a living body.

For example, glucose concentration in blood is referred to as a blood glucose level and is widely used as an index of diabetes and the like. Aqueous humor which has substantially the same components as those of serum also includes many of optically active substances which have optical activity and include glucose, protein such as albumin and globulin, and ascorbic acid. It is known that there is a correlationship between glucose concentration in the blood and glucose concentration in the aqueous humor.

The aqueous humor has high transparency. Thus, if the glucose concentration of the aqueous humor is allowed to be measured by using optical activity, a measuring method of noninvasive glucose concentration may be used.

However, it is known that optical rotations $\alpha$ varies depending on the type of an optically active substance. If the measurement target 13 in which a plurality of optically active substances is mixed is irradiated with linear polarized light, optical rotation $\alpha$ of each of the optically active substances is not observed, but, observed optical rotation $\alpha_M$ influenced by the optical rotations $\alpha$ of all of the optically active substances included in the measurement target is observed.

For example, in a case where glucose concentration is obtained by using the optical activity, it is necessary that a signal (concentration, optical rotation $\alpha$, and the like) corresponding to glucose which is set as a target, is separated from the observed optical rotation $\alpha_M$.

In the following descriptions, regarding the measurement target 13 included in a plurality of optically active substances, a method of calculating concentration of an optically active substance which is set to be obtained, from the measured observed optical rotation $\alpha_M$ will be described.

(Optical Rotation $\alpha$)

Firstly, the optical rotation $\alpha$ will be described.

Regarding the measurement target 13 which includes a certain single optically active substance, the optical rotation $\alpha$ for the wavelength $\lambda$ is represented by a formula (1). That is, the optical rotation $\alpha$ (deg) is represented by the product of specific rotation $[\alpha]$ (deg/(dm·g/ml)), optical path length L (dm), and concentration C (g/ml). The specific rotation $[\alpha]$ does not include concentration C of the optically active substance or the optical path length L. The specific rotation $[\alpha]$ is a constant specific to the optically active substance under a constant temperature.

$$\alpha = [\alpha] \cdot L \cdot C \quad \text{Formula (1)}$$

Figure 2:
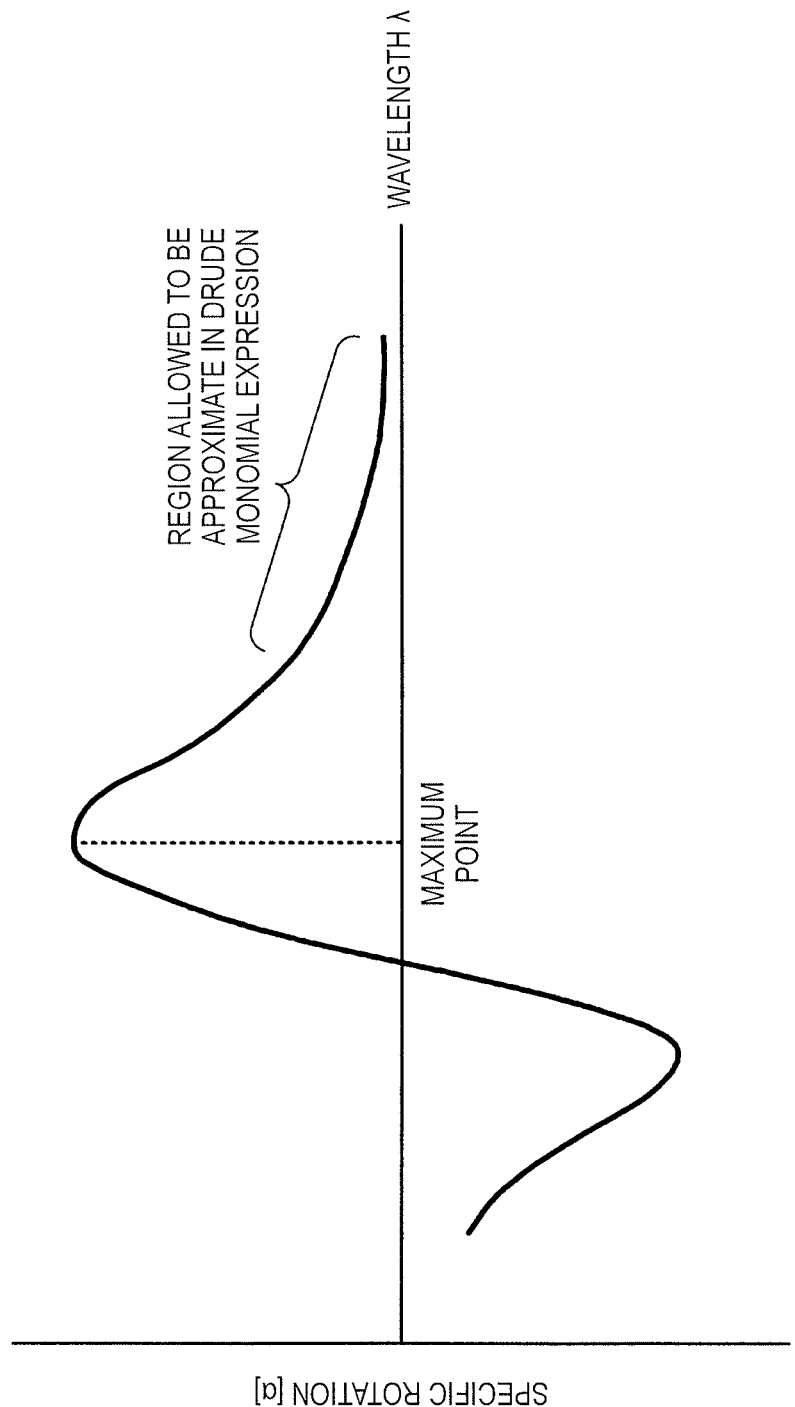
FIG. 2 is a diagram illustrating dependence of a specific rotation [α] on a wavelength λ.

FIG. 2 is a diagram illustrating dependence of the specific rotation $[\alpha]$ on the wavelength $\lambda$. The wavelength dependence of the specific rotation $[\alpha]$ is referred to as optical rotatory dispersion.

The specific rotation $[\alpha]$ may be represented in a wavelength region which has a length longer than a length between the maximum point and the minimum point, by a monotone-decreasing or monotone-increasing Drude monomial expression. The Drude monomial expression is an example of a function representing the optical rotatory dispersion of an optically active substance. The Drude monomial expression is a nonlinear function represented by a formula (2). In FIG. 2, the Drude monomial expression is illustrated as a monotone-decreasing function in a wavelength region over the maximum point. Here, "$\lambda$" is a variable, and "A" and "$\lambda_0$" are constants specific to the optically active substance (inherent value for defining characteristics of optical rotatory dispersion in the optically active substance).

$$[\alpha] = \frac{A}{\lambda^2 - \lambda_0^2} \quad \text{Formula (2)}$$

In a case where the measurement target 13 includes a plurality of optically active substances, the observed optical rotation $\alpha_M$ is represented by a formula (3). That is, the observed optical rotation $\alpha_M$ observed for the measuring target substance 13 including a plurality of optically active substances is described by adding optical rotations $\alpha_i$ of the optically active substances, in which the specific rotation $[\alpha]$ is represented by the Drude monomial expression of the formula (2). In other words, the observed optical rotation $\alpha_M$ is represented by the sum of a function representing wavelength dependence of the optical rotation of each of the optically active substances. As an example, the function is represented by the product of the Drude monomial expression and the concentration, or the product of the Drude monomial expression, the concentration, and the optical path length, and the like. Regarding inherent values $A_i$ and $\lambda_i$ of the optically active substances, a case of being known and a case of not being known are provided.

Here, in a case where the measurement target 13 includes a plurality of optically active substances, regarding each of the optically active substances, indication as optical rotation concentration $C_i$, specific rotation $[\alpha_i]$, inherent values $A_i$ and $\lambda_i$ is performed. Instead of a subscript of "i", a sign associated with the name of the optically active substance may be used. For example, in a case of glucose, a subscript of "g" and the like may be used. Because the optical path length L is determined by the measurement target 13, the optical path lengths L for the optically active substances are the same as each other.

$$\alpha_M = L \cdot \sum_i ([\alpha_i] \cdot C_i) = L \cdot \sum_i \left( \frac{A_i}{\lambda^2 - \lambda_i^2} \cdot C_i \right) \qquad \text{Formula (3)}$$

In a case where the measurement target 13 includes only glucose and albumin as the optically active substances, the observed optical rotation $\alpha_M$ is represented by a formula (4). That is, the observed optical rotation $\alpha_M$ is represented by the sum of a function representing wavelength dependence of optical rotation of glucose, and a function representing wavelength dependence of optical rotation of albumin. Here, $A_g$ and $\lambda_g$ are inherent values of the glucose, and $A_a$ and $\lambda_a$ are inherent values of the albumin. The glucose corresponds to concentration $C_g$ (glucose concentration $C_g$), and the albumin corresponds to concentration $C_a$ (albumin concentration $C_a$).

$$\alpha_M = \alpha_g + \alpha_a = L \cdot \left( \frac{A_g}{\lambda^2 - \lambda_g^2} \cdot C_g + \frac{A_a}{\lambda^2 - \lambda_a^2} \cdot C_a \right) \qquad \text{Formula (4)}$$

Figure 3:
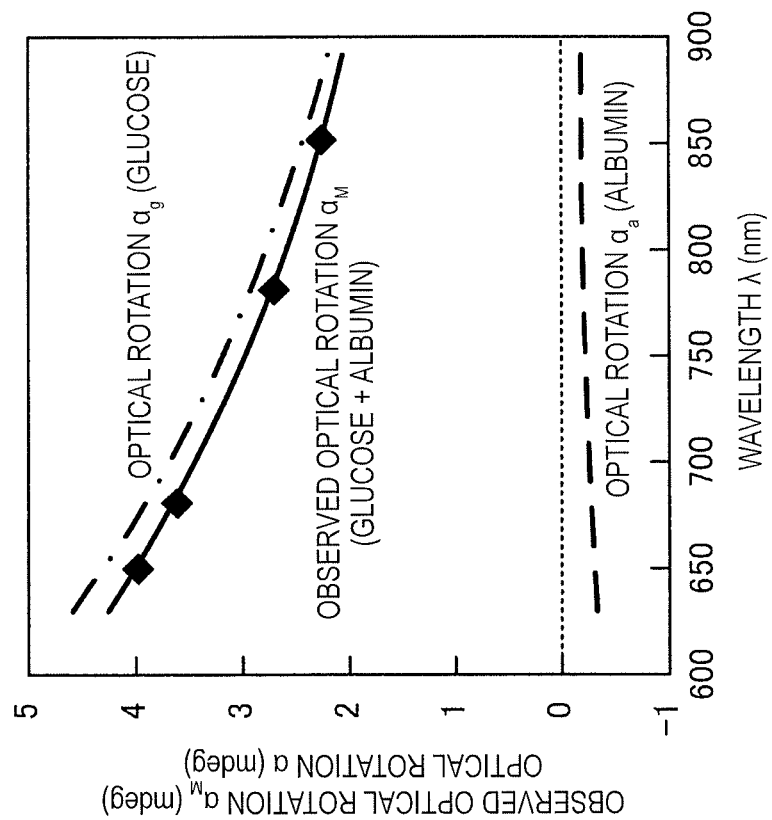
FIG. 3 is a diagram showing that an observed optical rotation $\alpha_M$ corresponds to the sum of an optical rotation $\alpha_g$ of glucose and an optical rotation $\alpha_a$ of albumin in a case where a measurement target includes the glucose and the albumin as an optically active substance.

FIG. 3 is a diagram illustrating that the observed optical rotation $\alpha_M$ is the sum of optical rotation $\alpha_g$ of the glucose, and optical rotation $\alpha_a$ of the albumin in a case where the measurement target 13 includes glucose and albumin as optically active substances.

Since the glucose shows clockwise optical activity (dextro-rotatory) and the albumin shows counterclockwise optical activity (levo-rotatory), as illustrated in FIG. 3, the optical rotation $\alpha_g$ of the glucose is positive and is monotone-decreasing for the wavelength $\lambda$. The optical rotation $\alpha_a$ of the albumin is negative, and is monotone-increasing for the wavelength $\lambda$.

As illustrated in FIG. 3, the observed optical rotation $\alpha_M$ is expressed by the sum of the optical rotation $\alpha_g$ of the glucose and the optical rotation $\alpha_a$ of the albumin.

In an example of FIG. 3, glucose has an influence on the observed optical rotation $\alpha_M$, larger than that of albumin. As expressed in the formula (1), the optical rotation $\alpha$ is determined by the product of the optical path length L, the specific rotation $[\alpha]$, and the concentration C. Thus, in FIG. 3, the glucose has a large specific rotation $[\alpha]$ and/or high concentration C, in comparison to albumin.

As illustrated in FIG. 3, in the aqueous humor, generally, glucose has an influence on the observed optical rotation $\alpha_M$, larger than that of albumin, and the glucose and the albumin have large specific rotation $[\alpha]$ and high concentration C, in comparison to other optically active substances.

(Calculation Method of Concentration $C_i$ of Optically Active Substance)

Next, regarding the measurement target 13 including a plurality of optically active substances, a method in which concentration $C_i$ of an optically active substance wanted to be obtained is calculated from the observed optical rotation $\alpha_M$ will be described. In the embodiment, as expressed by the formula (3), at least the concentration $C_i$ of the optically active substance wanted to be obtained is set to have a unknown value by using a formula (theoretical formula) which represents wavelength dependence of the optical rotation of the measurement target 13, and the concentration $C_i$ is calculated by a nonlinear least-squares method.

For example, in a case where the aqueous humor is assumed to be the measurement target 13, it is considered that at least 15 types or more of dextro-rotatory and levo-rotatory optically active substances are mixed to each other in the aqueous humor. Examples of the optically active substances in the aqueous humor include ascorbic acid, lactic acid, glucose, alanine, arginine, cysteine, glutamic acid, histidine, leucine, isoleucine, lysine, serine, valine, albumin, and globulin.

Thus, it is considered that a method of calculating the concentration $C_i$ of a specific optically-active substance such as glucose is employed, based on the formula expressed by the sum of the optical rotations $\alpha_i$ of all of the about 15 types of optically active substances, as expressed in the formula (3).

However, since the aqueous humor is in the eyeball of a person, and easy collection of substances drained to the outside of a body is not possible in a case of the tear, the urine, and the like, the accurate examination for the type of the included optically active substance is difficult, and is not clear. Since it is considered that the type or the concentration ratio of the optically active substance included in the aqueous humor is also changed due to a life habit of a person or dose of medicine, it is considered that calculation with desired accuracy is difficult even when, simply, the concentration $C_i$ of a specific optically-active substance such as the glucose is calculated based on the formula expressed by the sum of the optical rotations $\alpha_i$ of all of the about 15 types of optically active substances.

Thus, in the embodiment, numerical calculation is performed as follows. The sum of the optical rotation $\alpha_i$ of the specific optically-active substance and the optical rotation $\alpha_x$ of a collection of the remaining optically-active substances is obtained. The observed optical rotation $\alpha_M$ by the measurement target 13 including the plurality of optically active substances is caused to be approximate to the obtained sum, and inherent values for the remaining optically-active substances are set to an unknown value.

That is, as expressed in a formula (5), the observed optical rotation $\alpha_M$ is approximate to the sum of the optical rotation $\alpha_i$ for the specific optically-active substance and the optical rotation $\alpha_x$ for the collection of the remaining optically-active substances. In other words, the observed optical rotation $\alpha_M$ is set to the sum of the sum of functions which include the Drude monomial expression and represent optical rotatory dispersion for specific optically-active substances, and X(λ, A) representing optical rotatory dispersion for the collection of wavelength dependence of the optical rotations of the remaining optically-active substances.

Here, "n" indicates the total number of optically active substances included in the measurement target 13. "k" indicates the number of specific optically-active substances among all of the optically active substances included in the measurement target 13. Thus, 1≤k<n is satisfied. For example, in a case where the measurement target 13 includes 15 types of optically active substances, n=15 is satisfied. Regarding the specific optically-active substance, concentration for a substance having a large degree of an influence of the measurement target 13 on the observed optical rotation $\alpha_M$ (substance in which an absolute value of specific rotation is large) is calculated with high accuracy. Thus, if a substance having a largest degree of an influence is set to be included, accuracy in the calculated concentration for the substance is improved. In a case where a plurality of substances are selected as the specific optically-active substances, the plurality of substances may be selected in order of the substances having a large degree of an influence.

At least one of the specific optically-active substances may be an optically active substance wanted to obtain concentration. The concentration of the optically active substance wanted to obtain concentration is set to have an unknown value. The inherent value of the optically active substance wanted to obtain concentration is set to have a known value or an unknown value in a certain limited range, as will be described later. Regarding X(λ, A), at least one of inherent values of the remaining optically-active substance is set to be an unknown value.

As will be described later, in a case where it is known that X(λ, A) proportional to the optical rotation $\alpha_x$ of the plurality of remaining optically active substances has a small influence on the observed optical rotation $\alpha_M$, X(λ, A) may be set to "0".

$$\alpha_M = L \cdot \sum_{i=1}^{n} \alpha_i \quad \text{Formula (5)}$$

$$= L \cdot \left( \sum_{i=1}^{k} \alpha_i + \alpha_x \right)$$

$$= L \cdot \left( \sum_{i=1}^{k} \frac{A_i}{\lambda^2 - \lambda_i^2} \cdot C_i + X(\lambda, A) \right)$$

For example, in a case where the measurement target 13 is set to include 15 types of the optically active substances, and glucose and albumin are set as optically active substances wanted to obtain concentration in the 15 types of the optically active substances, a formula (6) is used as the formula (5). A first term in the formula (6) corresponds to optical rotation $\alpha_g$ of the glucose. A second term in the formula (6) corresponds to optical rotation $\alpha_a$ of the albumin. A third term therein corresponds to optical rotation $\alpha_x$ of a collection of the remaining optically-active substance other than the glucose and the albumin. $A_x$ and $\lambda_x$ in the third term correspond to constants for defining a collection of inherent values of the remaining optically-active substances. $C_x$ corresponds to concentration thereof.

For example, in a case where the concentration $C_g$ of the glucose is obtained, the first term corresponds to a first function (nonlinear function), and the second term and the third term correspond to a second function (nonlinear function). In a case where the concentration $C_g$ of the glucose and the concentration $C_a$ of the albumin are obtained, the first term and the second term correspond to the first function, and the third term corresponds to the second function. That is, a function relating to the concentration of the first optically-active substance is an example of the first function. A function relating to the concentration of the second optically-active substance is an example of the second function.

$$\alpha = \alpha_g + \alpha_a + \alpha_x \propto \frac{A_g}{\lambda^2 - \lambda_g^2} \cdot C_g + \frac{A_a}{\lambda^2 - \lambda_a^2} \cdot C_a + X(\lambda, A) \quad \text{Formula (6)}$$

$$= \frac{A_g}{\lambda^2 - \lambda_g^2} \cdot C_g + \frac{A_a}{\lambda^2 - \lambda_a^2} \cdot C_a + \frac{A_x}{\lambda^2 - \lambda_x^2} \cdot C_x$$

Figure 4:
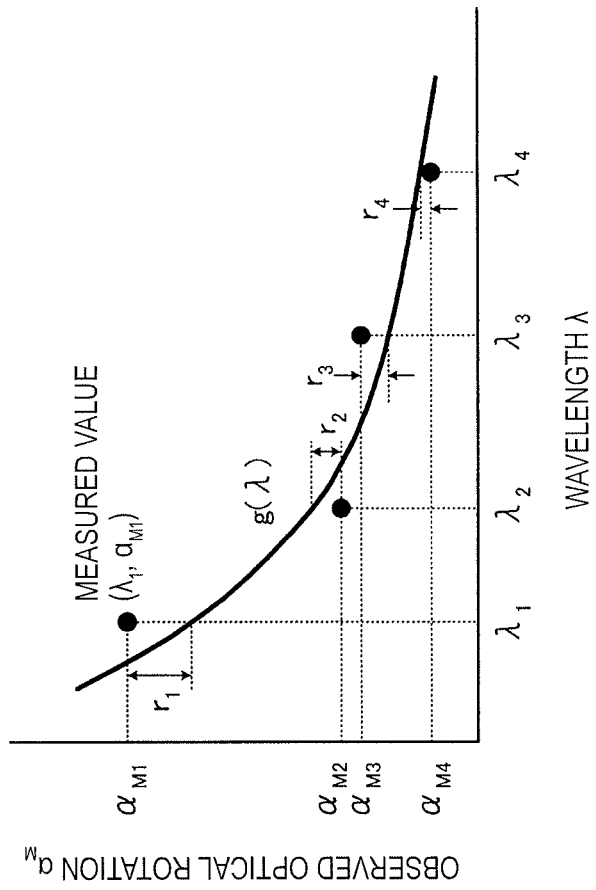
FIG. 4 is a diagram illustrating a method of obtaining a function g(λ) based on the observed optical rotation $\alpha_M$ with respect to a plurality of wavelengths λ, in such a manner a function is applied by using a nonlinear least-squares method.

FIG. 4 is a diagram illustrating a method of obtaining a function g(λ) based on the observed optical rotation $\alpha_M$ with respect to a plurality of wavelengths λ, in such a manner a function is applied by using a nonlinear least-squares method. The function g(λ) is a formula (theoretical formula) representing optical rotation of the measurement target 13, and corresponds to the formula (5). However, here, general setting as the function g(λ) is performed.

As illustrated in FIGS. 2 and 3, wavelength dependence of the observed optical rotation $\alpha_M$ on the wavelength λ is nonlinear. Thus, function application of the function g(λ) is performed by using the nonlinear least-squares method. That is, while a numerical value is applied to the unknown value of the concentration $C_i$ and the like wanted to be obtained, the function g(λ) which causes the sum of squares to be minimum is obtained.

As illustrated in FIG. 4, it is assumed that measured values (observed optical rotation $\alpha_{Mj}$ ($\alpha_{M1}$, $\alpha_{M2}$, $\alpha_{M3}$, and $\alpha_{M4}$) which respectively correspond to wavelengths λ ($\lambda_1$, $\lambda_2$, $\lambda_3$, and $\lambda_4$) are provided. If the corresponding measured values are provided, a difference $r_j$ between the function g($\lambda_j$) and the measured value (observed optical rotation $\alpha_{Mj}$) is represented by a formula (7). The sum of squares of differences $r_j$ is represented by a formula (8). A general form of the sum of squares is represented by a formula (9). The formula (9) is an objective function representing a difference between a true value (theoretical value) and a calculated value which will be described later.

$$r_1 = g(\lambda_1) - \alpha_{M1} \quad \text{Formula (7)}$$
$$r_2 = g(\lambda_2) - \alpha_{M2}$$
$$r_3 = g(\lambda_3) - \alpha_{M3}$$
$$r_4 = g(\lambda_4) - \alpha_{M4}$$

$$r_1^2 + r_2^2 + r_3^2 + r_4^2 \quad \text{Formula (8)}$$

$$\sum_{j=1}^{\text{NUMBER OF WAVELENGTHS}} [g(\lambda_j) - \alpha_{Mj}]^2 \quad \text{Formula (9)}$$

In the nonlinear least-squares method, the unknown value is set and application to a function is performed, such that the sum of squares of differences between the function g($\lambda_j$) and observed optical rotation $\alpha_{Mj}$ which is the measured value is caused to be minimum. As this method, an algorithm such as the Levenberg-Marquardt method, a quasi-Newton method, and a conjugate gradient method is used.

Here, the concentration C of an optically active substance wanted to be obtained is calculated by using the Levenberg-Marquardt method. The Levenberg-Marquardt method is developed for improving convergence instability of a solution of the Gauss•Newton method, and is widely used as an algorithm of the nonlinear least-squares method. Since the Levenberg-Marquardt method is a well-known method, descriptions thereof will be omitted.

A plurality of observed optical rotations $\alpha_M$, that is, observed optical rotation $\alpha_M$ for two or more wavelengths $\lambda$ are used as the measurement data. As the number of wavelengths $\lambda$ is increased, accuracy for the obtained unknown value is improved. However, if the number of wavelengths $\lambda$ is large, time to perform the numerical calculation is taken. Accordingly, the number of wavelengths $\lambda$ may be selected in accordance with a situation.

Here, the Levenberg-Marquardt method is used, but other algorithms may be applied.

Instead of such a least-squares method, the concentration of an optically active substance wanted to be obtained may be calculated by solving a simultaneous equation. In the simultaneous equation, the number of wavelengths $\lambda$ used in measurement is required to match with the number of unknown values. In the function application with the Levenberg-Marquardt method by using the nonlinear least-squares method, the concentration C of an optically active substance wanted to be obtained may be calculated even when the number of wavelengths $\lambda$ used in measurement does not match with the number of unknown values. That is, as long as the least-squares method is employed, the number of wavelengths $\lambda$ used in measurement may be smaller or larger than the number of unknown values.

In the following descriptions, calculation examples in which the glucose concentration $C_g$ is calculated through simulation will be described.

Here, concentration (calculated value) $C_{gc}$ of the glucose in a measurement target 13 in which 19 types of optically active substances including glucose were mixed was calculated. The calculation was performed from observed optical rotation $\alpha_M$ for a plurality of wavelengths $\lambda$ by using the nonlinear least-squares method with the Levenberg-Marquardt method. The calculated concentration $C_{gc}$ was compared to concentration (true value) $C_{gr}$ of the glucose included (mixed) in the measurement target 13.

The types and concentrations $C_i$ of optically active substances are set in a recognizable range, so as to cause the measurement target 13 to be approximate to the aqueous humor of a person. Since there is a variation in a person, three conditions of an upper limit, a lower limit, and the middle having a probability were set. In FIGS. 5 to 8 which will be described later, the three conditions are represented by signs of ○, □, and Δ, respectively.

Calculation Example 1

Figures 5A, 5B:
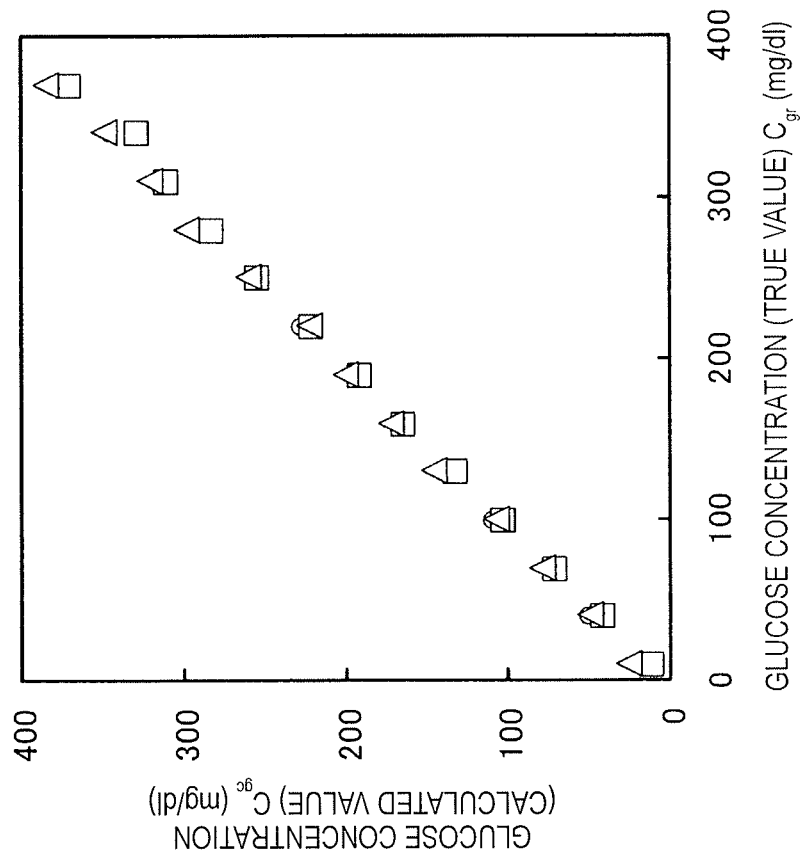
FIG. 5A is a diagram illustrating Calculation Example 1 in which glucose concentration $C_g$ is calculated from the observed optical rotation $\alpha_M$ and illustrates a relationship between the wavelength λ and the observed optical rotation $\alpha_M$.
FIG. 5B is a diagram illustrating Calculation Example 1 in which glucose concentration $C_g$ is calculated from the observed optical rotation $\alpha_M$ and illustrates a relationship between glucose concentration (true value) $C_{gr}$ and glucose concentration (calculated value) $C_{gc}$.

FIGS. 5A and 5B are diagrams illustrating Calculation Example 1 in which the glucose concentration $C_g$ is computed from the observed optical rotation $\alpha_M$. FIG. 5A is a diagram illustrating a relationship between the wavelength $\lambda$ and the observed optical rotation $\alpha_M$. FIG. 5B is a diagram illustrating a relationship between the glucose concentration (true value) $C_{gr}$ and the glucose concentration (calculated value) $C_{gc}$.

In Calculation Example 1, the glucose concentration $C_g$ in a measurement target 13 in which 19 types of optically active substances including glucose were mixed was computed by using the formula (6).

Here, in the formula (6), glucose concentration $C_g$, albumin concentration $C_a$, an inherent value $A_a$ of albumin, and an inherent value $\lambda_x$ which is a constant in $X(\lambda, A)$ obtained by collecting the remaining optically-active substances other than glucose and albumin were set to unknown values, and the product of $A_x$ and $C_x$ in the $X(\lambda, A)$ was set to one unknown value.

Inherent values $A_g$ and $\lambda_g$ of the glucose and an inherent value $\lambda_a$ of the albumin were set to known values, and were respectively set to $1.72 \times 10^7$, 150, and 250.

Four wavelengths $\lambda$ illustrated in FIG. 5A were used in measuring the observed optical rotation $\alpha_M$. Observed optical rotation $\alpha_{M1}$ (2.89 mdeg) was obtained for a wavelength $\lambda_1$ (410 nm). Observed optical rotation $\alpha_{M2}$ (2.79 mdeg) was obtained for a wavelength $\lambda_2$ (420 nm). Observed optical rotation $\alpha_{M3}$ (2.60 mdeg) was obtained for a wavelength $\lambda_3$ (440 nm). Observed optical rotation $\alpha_{M4}$ (2.33 mdeg) was obtained for a wavelength $\lambda_4$ (470 nm). Resolving power of the observed optical rotation $\alpha_M$ could be measured to two decimal places.

As known from the above result, the observed optical rotation $\alpha_M$ performs monotone decreasing in a wavelength range from the wavelength $\lambda_1$ (410 nm) to the wavelength $\lambda_4$ (470 nm).

Computation was started by setting an initial value of the glucose concentration $C_g$ to 500 mg/dl.

As illustrated in FIG. 5B, a proportional relationship is obtained between the glucose concentration (calculated value) $C_{gc}$ calculated by using the nonlinear least-squares method with the Levenberg-Marquardt method, and the glucose concentration (true value) $C_{gr}$, in a range in which the glucose concentration (true value) $C_{gr}$ is from 0 mg/dl to 400 mg/dl. The difference (variation) in the three conditions (○, □, and Δ) is smaller than the value of the glucose concentration $C_g$. That is, it is possible to calculate the glucose concentration $C_g$ of the measurement target 13 in which the 19 types of optically active substances including glucose are mixed, from the observed optical rotation $\alpha_M$ with high accuracy.

As described above, in a case where the types or a concentration ratio of the remaining optically-active substances included in the measurement target 13, such as the aqueous humor is not clear, it is considered that concentration calculation is difficult at a glance. However, as in the calculation example, inherent values in the $X(\lambda, A)$ are set to unknown values, and thus the concentration may be calculated with desired accuracy.

In the above computation, the albumin inherent value $A_a$ is set to an unknown value, but may be set to a known value. For example, in a case where the albumin concentration $C_a$ itself is concentration wanted to be obtained, a known value is used as the albumin inherent value $A_a$. In a case where the albumin concentration $C_a$ itself is not concentration wanted to be obtained, the product of the albumin concentration $C_a$ and the albumin inherent value $A_a$ may be set to one unknown value.

That is, in the above computation, the number of unknown values is set to 5. However, the number of unknown values may be smaller than 5 or more than 5.

The number of the wavelengths $\lambda$ is set to 4. However, a plurality of wavelengths $\lambda$ may be provided. The number of wavelengths $\lambda$ may be set to 2 or 3. The number of wavelengths $\lambda$ may be more than 4.

Further, in the numerical calculation, it is necessary that an initial value for the unknown value is set. In Example 1, 500 mg/dl is set to the glucose concentration $C_g$ as the initial value. However, the glucose concentration $C_g$ may be more than or smaller than 500 mg/dl.

Calculation Example 2

In Calculation Example 2, optical rotation $\alpha_x(X(\lambda, A))$ by the remaining optically-active substances other than glucose and albumin was set to be "0" in the formula (6). That is, instead of the formula (6), a formula (10) was used. The formula (10) is the formula (4).

$$\alpha_M = \alpha_g + \alpha_a = L \cdot \left( \frac{A_g}{\lambda^2 - \lambda_g^2} \cdot C_g + \frac{A_a}{\lambda^2 - \lambda_a^2} \cdot C_a \right) \quad \text{Formula (10)}$$

Figures 6A, 6B:
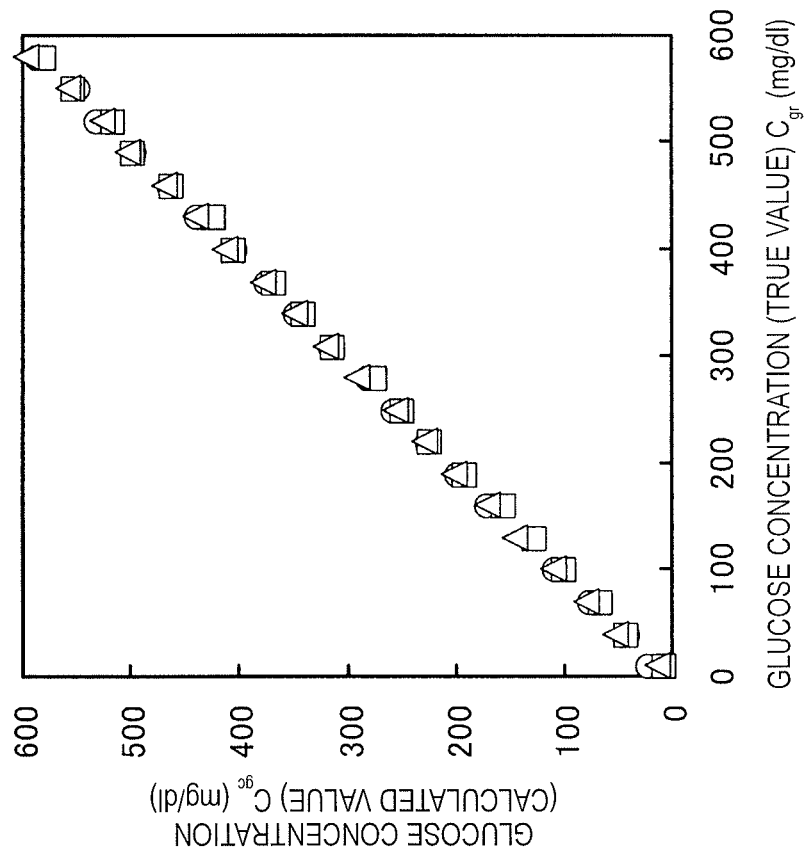
FIG. 6A is a diagram illustrating Calculation Example 2 in which the glucose concentration $C_g$ is computed from the observed optical rotation $\alpha_M$ by using a formula (10) and illustrates a relationship between the wavelength λ and the observed optical rotation $\alpha_M$.
FIG. 6B is a diagram illustrating Calculation Example 2 in which the glucose concentration $C_g$ is computed from the observed optical rotation $\alpha_M$ by using a formula (10) and illustrates a relationship between the glucose concentration (true value) $C_{gr}$ and the glucose concentration (calculated value) $C_{gc}$.

FIGS. 6A and 6B are diagrams illustrating Calculation Example 2 in which the glucose concentration $C_g$ is computed from the observed optical rotation $\alpha_M$ by using the formula (10). FIG. 6A is a diagram illustrating a relationship between the wavelength $\lambda$ and the observed optical rotation $\alpha_M$. FIG. 6B is a diagram illustrating a relationship between the glucose concentration (true value) $C_{gr}$ and the glucose concentration (calculated value) $C_{gc}$.

The glucose concentration $C_g$, the albumin concentration $C_a$, and the inherent value $A_a$ of the albumin were set to have unknown values, and known values were used in the inherent values $A_g$ and $\lambda_g$ of the glucose and the inherent value $\lambda_a$ of the albumin. Since $A_a$ and $C_a$ are simple products, a combination may be set to be one unknown value.

The four wavelengths illustrated in FIG. 6A were used in measuring the observed optical rotation $\alpha_M$. These four wavelengths were the same as the four wavelengths illustrated in FIG. 5A. However, resolving power of the observed optical rotation $\alpha_M$ for the wavelengths $\lambda$ was set to have one decimal place. This is because the obtained observed optical rotation $\alpha_M$ is assumed to be in submillimeter degree order, and because an influence of a case where obtaining the resolving power for the observed optical rotation $\alpha_M$ is difficult is clarified.

As illustrated in FIG. 6B, a proportional relationship is obtained between the glucose concentration (calculated value) $C_{gc}$ calculated by using the nonlinear least-squares method with the Levenberg-Marquardt method, and the glucose concentration (true value) $C_{gr}$, in a range in which the glucose concentration (true value) $C_{gr}$ is from 0 mg/dl to 600 mg/dl. The difference (variation) in the three conditions ($\circ$, $\square$, and $\Delta$) is smaller than the value of the glucose concentration $C_g$. That is, even when, in the formula (6), the optical rotation $\alpha_x(X(\lambda, A))$ of a collection of the remaining optically-active substances other than glucose and albumin is set to be "0", and the resolving power of the observed optical rotation $\alpha_M$ was set to have one decimal place, it is possible to calculate the glucose concentration $C_g$ from the observed optical rotation $\alpha_M$ for the measurement target 13 in which the 19 types of optically active substances including glucose are mixed, with high accuracy.

The inherent value $A_a$ of the albumin is set to an unknown value, but may be set to a known value. In a case where the inherent values $A_a$ and $\lambda_a$ of the albumin are set to known values, and in a case where the type or the concentration ratio of the optically active substance included in the aqueous humor is changed due to a life habit of a person or dose of medicine, a probability that the concentration calculation with desired accuracy is not possible is considered. In such a case, the formula (6) in Calculation Example 1 or a formula (11) in Calculation Example 3 which will be described later may be employed.

In a case where the formula (10) is applied to other measurement target other than the aqueous humor, a plurality of substances may be selected in order of the substances having a large degree of an influence on the observed optical rotation of the measurement target 13 (substance in which an absolute value of specific rotation is large), and optical rotations by other substances may be set to be "0".

FIGS. 7A-7D are diagrams illustrating a case where the glucose concentration $C_g$ is obtained from the observed optical rotation $\alpha_M$ by using the formula (10) and by using a wavelength $\lambda$ of a wavelength region different from that in a short wavelength region of 410 nm to 470 nm in FIGS. 6A and 6B. FIG. 7A illustrates a relationship between a wavelength $\lambda$ in a long wavelength region in a 660 nm to 850 nm, and the observed optical rotation $\alpha_M$. FIG. 7B illustrates a relationship between the glucose concentration (true value) $C_{gr}$ and the glucose concentration (calculated value) $C_{gc}$ in FIG. 7A. FIG. 7C illustrates a relationship between a wavelength $\lambda$ in the short wavelength region and the long wavelength region, and the observed optical rotation $\alpha_M$. FIG. 7D illustrates a relationship between the glucose concentration (true value) $C_{gr}$ and the glucose concentration (calculated value) $C_{gc}$ in FIG. 7C.

As illustrated in FIG. 7A, observed optical rotation $\alpha_{M5}$ (1.2 mdeg) was obtained for a wavelength $\lambda_5$ (660 nm). Observed optical rotation $\alpha_{M6}$ (1.1 mdeg) was obtained for a wavelength $\lambda_6$ (690 nm). Observed optical rotation $\alpha_{M7}$ (0.9 mdeg) was obtained for a wavelength $\lambda_7$ (780 nm). Observed optical rotation $\alpha_{M8}$ (0.7 mdeg) was obtained for a wavelength $\lambda_8$ (850 nm). The optical rotation $\alpha_M$ was set to have one decimal place.

As illustrated in FIG. 7A, the observed optical rotation $\alpha_M$ performs monotone decreasing in a wavelength range from the wavelength $\lambda_5$ (660 nm) to the wavelength $\lambda_8$ (850 nm). However, a change of the observed optical rotation $\alpha_M$ is smaller than that in a case where light having a short wavelength region illustrated in FIG. 6A is used.

As illustrated in FIG. 7B, a proportional relationship is obtained between the glucose concentration (calculated value) $C_{gc}$ and the glucose concentration (true value) $C_{gr}$, in a range in which the glucose concentration (true value) $C_{gr}$ is from 0 mg/dl to 600 mg/dl. However, the difference (variation) in the three conditions ($\circ$, $\square$, and $\Delta$) is larger than a case illustrated in FIG. 6B. It is considered that this is because a change of the observed optical rotation $\alpha_M$ for the wavelength $\lambda$ is small. That is, in FIG. 2, the reason is that the long wavelength region corresponds to a region of the wavelength $\lambda$, in which a change of the specific rotation $[\alpha]$ is small.

On the contrary, in FIG. 7C, the observed optical rotation $\alpha_{M3}$ (2.6 mdeg) for the wavelength $\lambda_3$ (440 nm), and the observed optical rotation $\alpha_{M4}$ (2.3 mdeg) for the wavelength $\lambda_4$ (470 nm) which are illustrated in FIG. 6A are used, and the observed optical rotation $\alpha_{M7}$ (0.9 mdeg) for the wavelength $\lambda_7$ (780 nm), and the observed optical rotation $\alpha_{M8}$ (0.7 mdeg) for the wavelength $\lambda_8$ (850 nm) which are illustrated in FIG. 7A are used. The observed optical rotation $\alpha_M$ performs monotone decreasing in a wavelength range from the wavelength $\lambda_3$ (440 nm) to the wavelength $\lambda_8$ (850 nm). The change of the observed optical rotation $\alpha_M$ is larger than that in a case where the short wavelength region illustrated in FIG. 6A is used, and that in a case where the long wavelength region illustrated in FIG. 7A is used.

As illustrated in FIG. 7D, similar to the cases illustrated in FIG. 6B and FIG. 7B, a proportional relationship is obtained between the glucose concentration (calculated value) $C_{gc}$, and the glucose concentration (true value) $C_{gr}$, in a range in which the glucose concentration (true value) $C_{gr}$ is from 0 mg/dl to 600 mg/dl. The difference (variation) in the three conditions (○, □, and Δ) is smaller than the case illustrated in FIG. 7B and the case illustrated in FIG. 6B. It is considered that this is because a change of the observed optical rotation $\alpha_M$ for the wavelength λ is large. That is, if wavelengths λ are selected so as to be included in a range from the short wavelength region to the long wavelength region such that the observed optical rotation $\alpha_M$ is changed largely, the accuracy in calculation of the concentration $C_i$ of an optically active substance wanted to be obtained is improved.

In order to improve the accuracy in calculation of the concentration $C_i$, the light source 11 may be configured by a semiconductor laser formed of a different semiconductor material such that a plurality of wavelengths λ is selected, for example, so as to include a range from the short wavelength region to the long wavelength region in the visible light wavelength region. As the light source 11 having a blue region in which the wavelength λ is from 400 nm to 500 nm, a semiconductor laser in which an active layer is formed of mixed crystals (GaN, AlGaInN, GaInN, and the like) of gallium nitride may be applied. As the light source 11 having a red region in which the wavelength λ is from 600 nm to 700 nm, a semiconductor laser in which an active layer is formed of mixed crystals (AlGaInP, GaInP, and the like) of gallium phosphide may be applied. As the light source 11 having a red region or an infrared region in which the wavelength λ is in the vicinity of 800 nm, a semiconductor laser in which an active layer is formed of mixed crystals (AlGaAs, GaAs, and the like) of gallium arsenide may be applied.

The semiconductor laser described here is an example, and a semiconductor laser corresponding to the wavelength λ may be selected and used.

The semiconductor laser is compact and has a narrow bandwidth, and thus contributes to reduction in the size of the concentration calculation system 1 of an optically active substance.

Calculation Example 3

In Calculation Example 3, the formula (11) was used. The formula (11) is obtained by substituting the optical rotation $\alpha_a$ for the albumin in the formula (10) with the optical rotation $\alpha_x$ described for a collection of the remaining optically-active substances other than the glucose. The collection of the remaining optically-active substances other than the glucose is set as concentration $C_x$, and the collection of the remaining optically-active substances other than the glucose is set as constants $A_x$ and $\lambda_x$, and thus single terms are used.

$$\alpha_M = \alpha_g + \alpha_x = L \cdot \left( \frac{A_g}{\lambda^2 - \lambda_g^2} \cdot C_g + \frac{A_x}{\lambda^2 - \lambda_x^2} \cdot C_x \right) \quad \text{Formula (11)}$$

Figures 8A, 8B:
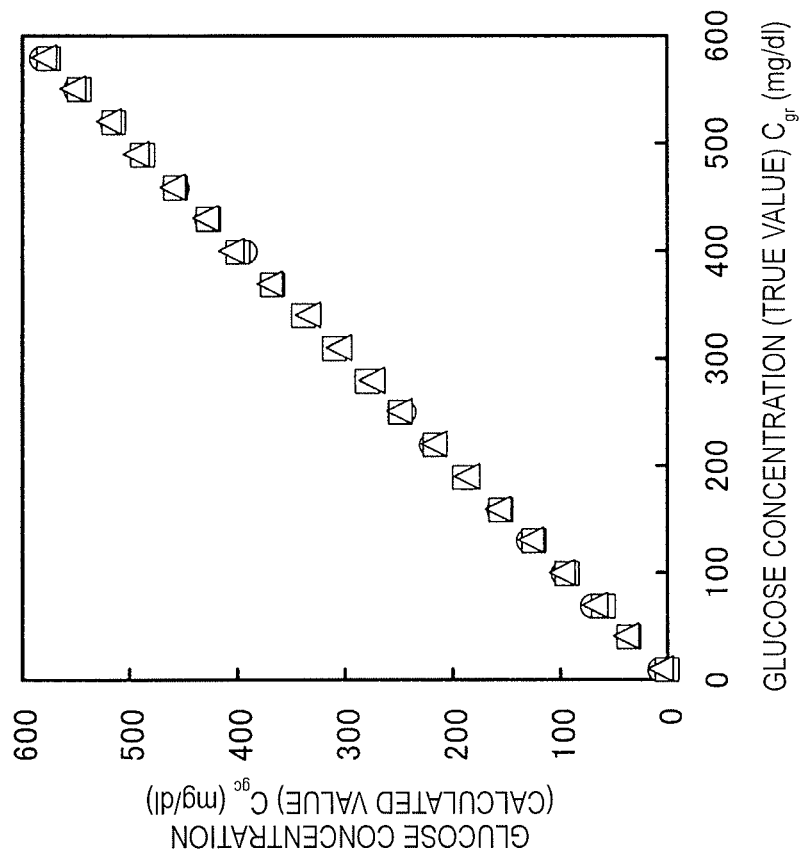
FIG. 8A is a diagram illustrating Calculation Example 3 in which the glucose concentration $C_g$ is obtained from the observed optical rotation $\alpha_M$ by using a formula (11) and illustrates a relationship between the wavelength λ and the observed optical rotation $\alpha_M$.
FIG. 8B is a diagram illustrating Calculation Example 3 in which the glucose concentration $C_g$ is obtained from the observed optical rotation $\alpha_M$ by using a formula (11) and illustrates a relationship between the glucose concentration (true value) $C_{gr}$ and the glucose concentration (calculated value) $C_{gc}$.

FIGS. 8A and 8B are diagrams illustrating Calculation Example 3 in which the glucose concentration $C_g$ is obtained from the observed optical rotation $\alpha_M$ by using a formula (11). FIG. 8A illustrates a relationship between the wavelength λ and the observed optical rotation $\alpha_M$. FIG. 8B illustrates a relationship between the glucose concentration (true value) $C_{gr}$ and the glucose concentration (calculated value) $C_{gc}$.

The glucose concentration $C_g$, the concentration $C_x$ for the collection of the remaining optically-active substances other than the glucose, and the constants $A_x$ and $\lambda_x$ for the collection of the remaining optically-active substances other than the glucose were set to unknown values. $1.72 \times 10^7$ and 150 were respectively used as the inherent values $A_g$ and $\lambda_g$ of the glucose. Since $A_x$ and $C_x$ are simple products, a combination of $A_x$ and $C_x$ was computed as one unknown value. A case where the product of the inherent value and the concentration is an unknown value in this manner is an example in which the inherent value is an unknown value.

Four wavelengths illustrated in FIG. 8A were used in measuring the observed optical rotation $\alpha_M$. These four wavelengths were the same as the four wavelengths illustrated in FIG. 7C. A wavelength region in which the difference of the observed optical rotation $\alpha_M$ became large was used.

As illustrated in FIG. 8B, a proportional relationship is obtained between the glucose concentration (calculated value) $C_{gc}$, and the glucose concentration (true value) $C_{gr}$, in a range in which the glucose concentration (true value) $C_{gr}$ is from 0 mg/dl to 600 mg/dl. The difference (variation) in the three conditions (○, □, and Δ) is small. That is, even when, in the formula (10), the optical rotation $\alpha_a$ of the albumin is set to be the optical rotation $\alpha_x$ of a collection of the remaining optically-active substances other than the glucose, it is possible to calculate the glucose concentration $C_g$ from the observed optical rotation $\alpha_M$ for the measurement target 13 in which 19 types of the optically active substances including the glucose, with high accuracy. In a case where the formula (11) is applied to other measurement target 13 other than the aqueous humor, a substance having a largest degree of an influence of the measurement target 13 on the observed optical rotation (substance in which the absolute value of the specific rotation is largest) may be selected, and a collection of the remaining optically-active substance may be set to be the optical rotation $\alpha_x$.

In the above computation, the inherent values $A_g$ and $\lambda_g$ of the glucose are set to $1.72 \times 10^7$ and 150. However, ranges of the inherent values $A_g$ and $\lambda_g$ may be designated. For example, in a case where the inherent values are changed by fluctuation in an environment such as a temperature, unknown values in a range predetermined considering the fluctuation, that is, unknown values in a certain limited range may be used. For example, the inherent value $\lambda_g$ may be in a range of 145 to 155. This is similar to a case (which will be described later) in which a restriction condition is provided for an unknown value.

In a case where the albumin concentration $C_a$ is wanted to be obtained instead of the glucose concentration $C_g$, a formula (12) may be used instead of the formula (11).

$$\alpha_M = \alpha_a + \alpha_x = L \cdot \left( \frac{A_a}{\lambda^2 - \lambda_a^2} \cdot C_a + \frac{A_x}{\lambda^2 - \lambda_x^2} \cdot C_x \right) \quad \text{Formula (12)}$$

As described above, the formula (6), the formula (10), and the formula (11) may be applied for the glucose assumed to be included in the aqueous humor which is set as an example of the measurement target 13.

In the above descriptions, an example in which the concentration is calculated by using the least-squares method is described. However, the concentration may be calculated by solving a simultaneous equation. In this case, the number of the wavelengths λ may be set to be the same as the number of unknown values in the simultaneous equation.

Since the formula (11) is simple, a computation time for the formula (11) is shorter than that for the formula (6). Thus, in a case where the computation time is wanted to be reduced, not the formula (6), but the formula (11) may be used. Regarding other measurement target 13, the optically active substance in the formula (6), the formula (10), and the formula (11) may be changed and used in accordance with the type of an optically active substance wanted to be obtained, or the type of an optically active substance included in the measurement target 13.

In the embodiment, as expressed in the formula (6) or the formula (11), an inherent value for defining characteristics of optical rotatory dispersion of optically active substances other than an optically active substance wanted to obtain concentration thereof is set to an unknown value. Thus, as with the aqueous humor, regarding measurement target 13 in which the types or the concentration ratio of optically active substances other than an optically active substance wanted to obtain concentration thereof is not clear, the concentration C of the optically active substance wanted to obtain concentration thereof is calculated.

As expressed in the formula (5), the observed optical rotation $\alpha_M$ is represented by the sum of nonlinear functions of the number smaller than the number of optically active substance included in the measurement target 13. That is, regarding a plurality of optically active substances other than the optically active substance wanted to obtain concentration thereof, a function in which a collection of wavelength dependence of optical rotations is expressed as a single term is used. Thus, it is not necessary that the formula is expressed by the sum of nonlinear functions which respectively correspond to all optically active substances included in the measurement target 13. Accordingly, the number of unknown value included in the formula is reduced. Thus, for example, the computation time may be reduced.

Even when the function application is performed by using the nonlinear least-squares method, and thus the number of unknown values is more than the number of wavelengths λ used in measurement, the concentration C of the optically active substance wanted to be obtained can be calculated. Thus, if the number of wavelengths λ used in measurement is set to be more than the number of the unknown values, the accuracy in the concentration calculation is increased in comparison to a case of being small.

In the above descriptions, the optical rotatory dispersion is approximate to the Drude monomial expression expressed in the formula (2). However, the optical rotatory dispersion may be approximate to other nonlinear functions which perform monotone decreasing or monotone increasing. In addition, if a wavelength in a wide range from the long wavelength region to the short wavelength region is not used, and, for example, a wavelength only in the long wavelength region or only in the short wavelength region is used, the inclination of specific rotation is closer to a straight line than a case where a wavelength in a wide range is used. Thus, in such a case, the concentration may be calculated by performing setting to be close to a linear function, and by using a linear least-squares method.

(Method of Improving Correlationship of Calculated Value)

The calculated value is required for improving a correlationship (proportional relationship) with the true value. Thus, a method of improving a correlationship of the calculated value with the true value will be described.

Local optimization computation by a gradient method such as the Levenberg-Marquardt method and a quasi-Newton method, which is used as a numerical calculation algorithm does not search for the minimum value of the function, but search for the minimum value in a certain region. Thus, if computation in an appropriate region is not possible, an obtained solution (calculated value) is largely different from the true value. Even when the given initial value (initially-estimated value) is used, an obtained solution (calculated value) may be largely different from the true value.

Even in such a case, the restriction condition for restricting a certain range is provided for the unknown value of the concentration C of an optically active substance, the inherent value, or the like. Thus, the calculated value and the true value match with each other, or are close to each other.

The calculated value and the true value also match with each other, or are close to each other by replacing the initial value (initially-estimated value) of the unknown value.

That is, the accuracy for the calculated value is improved.

Firstly, a case where the restriction condition is provided for the unknown value of the concentration C of an optically active substance, the inherent value, or the like will be described.

FIG. 9 is a diagram for a comparison between a case where a restriction condition for an unknown value is not provided, and a case where a restriction condition for an unknown value is provided when the glucose concentration (calculated value) $C_{gc}$ is calculated by using the formula (11). In FIG. 9, (a) in illustrates the case where a restriction condition for an unknown value is not provided. In FIG. 9, (b) and (c) illustrate the case where a restriction condition for an unknown value is provided. In FIG. 9, (a) to (c) illustrate a relationship between the glucose concentration (true value) $C_{gr}$ and the glucose concentration (calculated value) $C_{gc}$.

In (a) to (c) in FIG. 9, signs of ◇, □, △, ■, and ○ represent cases where a mixing ratio of optically active substances is different in the measurement target 13 in which 19 types of the optically active substances including glucose are mixed.

The initial value of the glucose concentration $C_{gc}$ which will be described later is set to 300 mg/dl.

In a case where the restriction condition is not provided in (a) in FIG. 9, correlation between the true value and the calculated value is obtained to a certain extent. However, calculated values (plotted points) are slightly widely dispersed.

In a case where the restriction condition in which $C_{gc}>0$ and $A_x<0$ are set is provided in (b) in FIG. 9, similar to the case in (a) in FIG. 9, calculated value (plotted points) are slightly widely dispersed.

However, in a case where the restriction condition in which $C_{gc}>0$, $A_x<0$, and $250 \leq \lambda_x \leq 300$ are set is provided in (c), differently from (a) (b) in FIG. 9, calculated value (plotted points) are hardly dispersed, and a correlationship (proportional relationship) between the glucose concentration (true value) $C_{gr}$ and the glucose concentration (calculated value) $C_{gc}$ is high.

As described above, if the restriction condition is provided for the unknown value of the concentration C of an optically active substance, the inherent value, or the like, a correlationship between the calculated value and the true value is increased. As illustrated in (b) and (c) FIG. 9, in a case where many unknown optically active substances are provided and the mixing ratio (concentration ratio) is unknown, giving an appropriate restriction condition is difficult.

Next, a case where an initial value of the unknown value of the concentration C of an optically active substance, the inherent value, or the like is replaced will be described. Here, a case where the initial value of the concentration C of an optically active substance is replaced will be described.

FIG. 10 is a diagram for a comparison between initial values of the glucose concentration (calculated value) $C_{gc}$ set when the glucose concentration (calculated value) $C_{gc}$ is calculated by using the formula (11). In FIG. 10, (a) illustrates a case where the initial value is 100 ml/dl. (b) illustrates a case where the initial value is 300 ml/dl. (c) illustrates a case where the initial value is 500 ml/dl.

Signs of ◇, □, △, ■, and ○ in (a) to (c) in FIG. 10 are the same as the signs in the cases in (a) to (c) in FIG. 9.

The restriction condition regarding the unknown value is set to be $C_{gc}>0$, $A_x<0$, and $250 \leq \lambda_x \leq 300$, that is, the same as that in (c) in FIG. 9.

In a case where the initial value of the glucose concentration $C_{gc}$ illustrated in (a) in FIG. 10 is set to 100 mg/dl, as illustrated in an area I, many calculated values (plotted points) are largely out from the proportional relationship (1:1) between the glucose concentration (true value) $C_{gr}$ and the glucose concentration (calculated value) $C_{gc}$. That is, the calculated values are largely diverged from true values.

On the contrary, in a case where the initial value of the glucose concentration $C_{gc}$ illustrated in (b) in FIG. 10 is set to 300 mg/dl, calculated values (plotted points) are distributed so as to be close to the proportional relationship between the glucose concentration (true value) $C_{gr}$ and the glucose concentration (calculated value) $C_{gc}$.

Further, in a case where the initial value of the glucose concentration $C_{gc}$ illustrated in FIG. 10(c) is set to 500 mg/dl, calculated values (plotted points) are distributed so as to be further close to the proportional relationship between the glucose concentration (true value) $C_{gr}$ and the glucose concentration (calculated value) $C_{gc}$.

As illustrated in FIG. 10(a), the calculated values are largely diverged from the true values by a manner of setting the initial value of the concentration C of an optically active substance. Thus, in the case where many unknown optically active substances are provided and the mixing ratio (concentration ratio) is unknown, giving an appropriate initial value is difficult.

In the embodiment, the restriction condition for the unknown value is not limited to a certain value or a certain range, and the concentration C of an optically active substance is set to be calculated under a plurality of restriction conditions (obtained by changing the restriction condition). Thus, a preferable calculated value is set as the concentration C of the optically active substance, among calculated values which are respectively obtained under the plurality of restriction conditions.

Similarly, the initial value for the unknown value is also not limited to a certain value, and the concentration C of an optically active substance is set to be calculated by using a plurality of initial values (obtained by changing the initial value). Thus, a preferable calculated value is set as the concentration C of the optically active substance, among calculated values which are respectively obtained by using the plurality of initial values.

Either or both of the restriction condition and the initial value for the unknown value are provided so as to be plural. That is, a combination of the restriction condition and the initial value may be provided so as to be plural, and the concentration C of the optically active substance may be calculated.

At this time, it is necessary that a calculated value which causes a difference between the true value and the calculated value to be small is set as a preferable calculated value. However, since the true value is not known, an index for selecting the preferable calculated value is required. Thus, here, the formula (9) which corresponds to the difference between the true value and the calculated value is set to be an objective function, and the preferable calculated value is set to be selected by the value of the objective function. As the value of the objective function represented by the formula (9) becomes small, the difference between the true value and the calculated value is small.

Thus, the formula (9) may be set as the objective function, values of the objective function of a plurality of restriction conditions, a plurality of initial values, or the like for the unknown value may be compared to each other, and thus the preferable calculated value may be selected.

FIG. 11 is a diagram illustrating an example in which a preferable calculated value is obtained from concentration C of an optically active substance, which is calculated under restriction conditions A and B. In FIG. 11, (a) illustrates a relationship between the glucose concentration (true value) $C_{gr}$ and the glucose concentration (calculated value) $C_{gc}$ in a case of the restriction condition A. In FIG. 11, (b) illustrates a relationship between the glucose concentration (true value) $C_{gr}$ and the glucose concentration (calculated value) $C_{gc}$ in a case of the restriction condition B. In FIG. 11, (c) is a table showing a relationship between the value of the objective function calculated for a measurement target 13 having certain glucose concentration $C_{gr}$ and the glucose concentration $C_{gc}$.

A restriction condition A in (a) in FIG. 11 corresponds to $C_{gc}>0$, $A_x<0$, and $200 \leq \lambda_x \leq 300$. An initial value of the glucose concentration $C_{gc}$ is set to 300 mg/dl. In the restriction condition A, correlation between the true value and the calculated value is obtained to a certain extent, but calculated values (plotted points) are slightly widely dispersed.

A restriction condition B in (b) in FIG. 11 corresponds to $C_{gc}>0$, $A_x<0$, and $250 \leq \lambda_x \leq 300$. The initial value of the glucose concentration $C_{gc}$ is set to 300 mg/dl. The restriction condition B is the same as in (c) in FIG. 9. In the restriction condition B, calculated values (plotted points) are not dispersed as much as in the restriction condition A, and the glucose concentration (true value) $C_{gr}$ and the glucose concentration (calculated value) $C_{gc}$ have a relation which is close to a proportional relationship.

That is, if the glucose concentration $C_{gc}$ is calculated by using the restriction condition B, the accuracy in the concentration calculation is improved in comparison to a case using the restriction condition A.

As illustrated in (c) in FIG. 11, regarding the measurement target 13 having certain glucose concentration $C_{gr}$, the value of the objective function, which is calculated in the restriction condition A is $3.5 \times 10^{-3}$, and the glucose concentration $C_{gc}$ is 230 mg/dl. On the contrary, the value of the objective function, which is calculated in the restriction condition B is $1.56 \times 10^{-5}$, and the glucose concentration $C_{gc}$ is 198 mg/dl.

Regarding the restriction condition A and the restriction condition B, the value of the objective function in the restriction condition B is smaller than that in the restriction condition A. That is, the difference between the true value and the calculated value is small. Thus, 198 mg/dl calculated under the restriction condition B may be selected as the glucose concentration $C_{gc}$.

FIGS. 11(a) and 11(b) illustrate that it is confirmed that, if the restriction condition B is selected, the difference between the true value and the calculated value is small. In FIG. 11, (c) illustrates that a calculated value which is closer to the true value is selected depending on the value of the objective function.

In the above descriptions, a case where two restriction conditions are provided as the restriction conditions A and B is described. However, three or more restriction conditions may be provided. In such a case, the concentration C of an optically active substance, which is calculated in other restriction condition in which the objective function has a smallest value may be selected. The concentration C of the optically active substance, which is calculated in a restriction condition in which the objective function has a largest value may be excluded, and other concentration C of an optically active substance, which is calculated in other restriction condition may be selected. In addition, a result obtained by performing calculation based on the other restriction condition may be used as the concentration C of the optically active substance, for example, other concentrations C of optically active substances, which are calculated in a restriction condition may be averaged, and the averaged concentration may be used as the concentration C of the optically active substance. A plurality of excluding restriction conditions of a restriction condition in which the objective function has a largest value, a restriction condition subsequent to the restriction condition in which the objective function has a largest value, and the like may be set.

In the above descriptions, a case where a plurality of restriction conditions are applied to the unknown value, and the calculation is performed is described. However, the above descriptions may be similarly applied to a case where calculation for one unknown value is performed by using a plurality of initial values, or a case where calculation for the unknown value is performed by using a plurality of combinations of the restriction conditions and the initial values. For example, as a case where the concentration C of an optically active substance, which is an example of the unknown value is calculated by using a plurality of initial values, the concentration C of the optically active substance may be calculated by using the plurality of initial values illustrated in (a) to (c) in FIG. 10, and a preferable calculated value may be selected.

Calculation for a parameter is performed by using a plurality of restriction conditions or a plurality of initial values, or the calculation is performed by using a combination of the plurality of restriction conditions and the plurality of initial values. Thus, a calculated value having a high correlationship with the true value is obtained.

Here, the concentration C (glucose concentration $C_{gc}$) of an optically active substance is calculated based on the formula (11). However, the calculation may be performed by using other formulas (6), (10), and (12).

(Data Processing Unit 30)

In the following descriptions, an example of the data processing unit 30 will be described.

Figure 12:
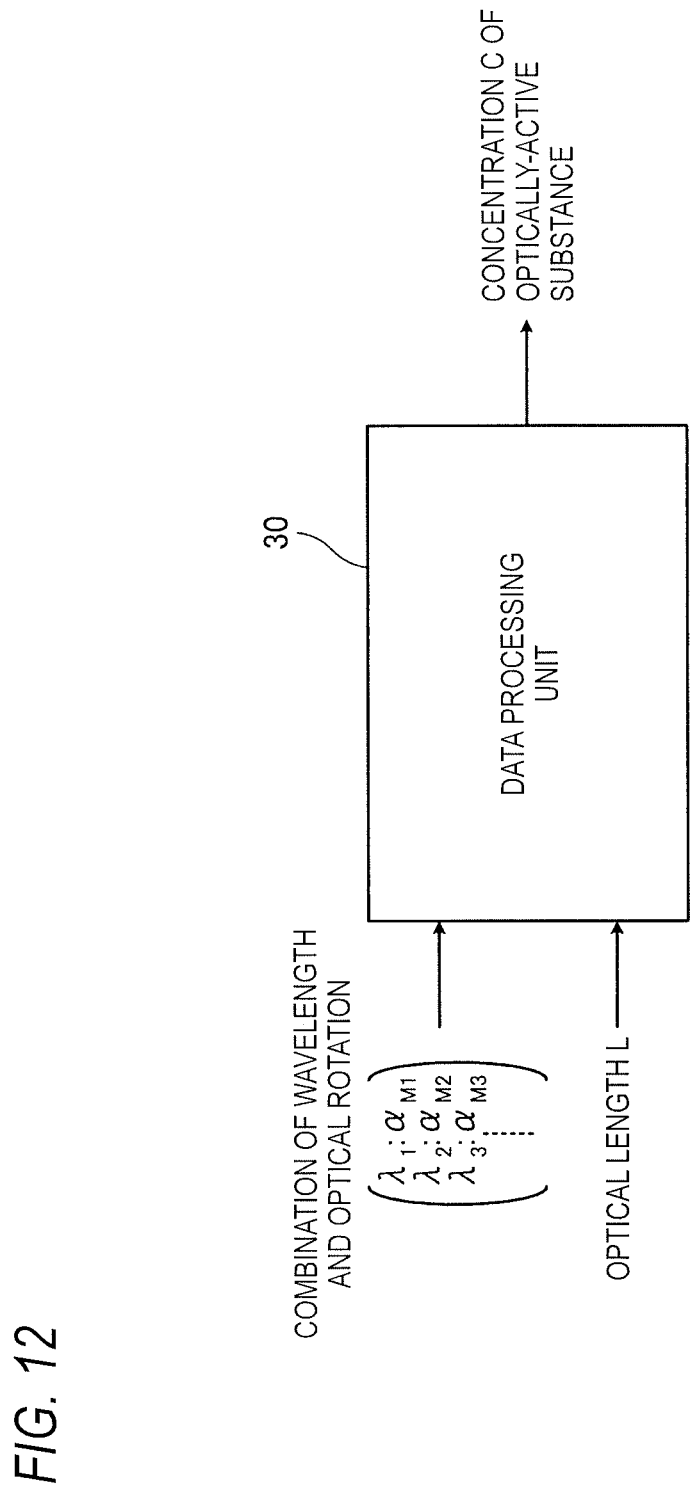
FIG. 12 is a diagram illustrating an outline of a data processing unit.

FIG. 12 is a diagram illustrating an outline of the data processing unit 30. The data processing unit 30 outputs the concentration C of an optically active substance set to be obtained from measurement data $(\lambda_1:\alpha_{M1}, \lambda_2:\alpha_{M2}, \lambda_3:\alpha_{M3}, \ldots)$ and an optical path length L. The measurement data is obtained by combining a wavelength $\lambda$ and an observed optical rotation $\alpha_M$ measured by using the wavelength $\lambda$.

Example 1

Figure 13:
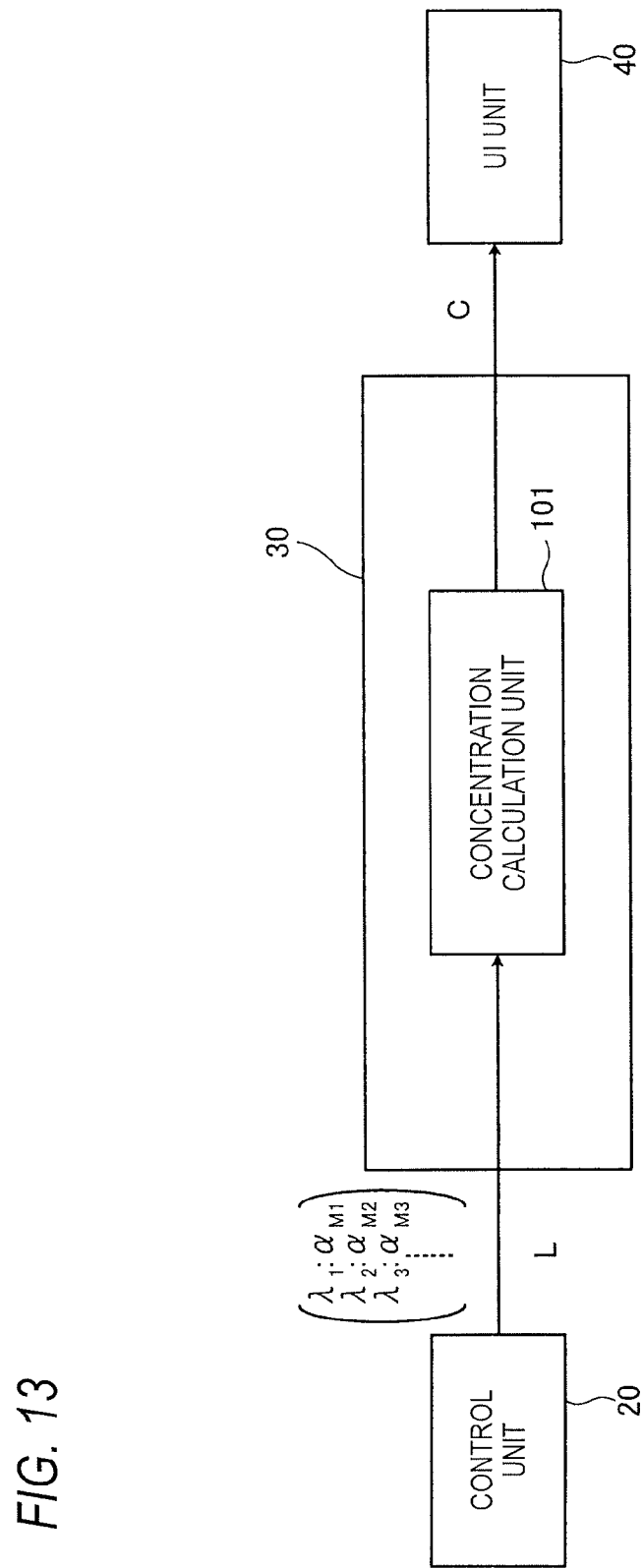
FIG. 13 is a diagram illustrating functional units of the data processing unit in Example 1.

FIG. 13 is a diagram illustrating functional units of the data processing unit 30 in Example 1.

The data processing unit 30 is connected to the control unit 20 and the UI unit 40. The data processing unit 30 includes a concentration calculation unit 101.

The concentration calculation unit 101 of the data processing unit 30 calculates the concentration C of an optically active substance based on the measurement data $\lambda_1:\alpha_{M1}$, $\lambda_2:\alpha_{M2}, \lambda_3:\alpha_{M3}, \ldots$) and the optical path length L which have been transmitted from the control unit 20. The measurement data is obtained by combining the wavelength $\lambda$ and the observed optical rotation $\alpha_M$. The concentration calculation unit 101 transmits the calculated concentration C of the optically active substance to the UI unit 40.

The concentration calculation unit 101 is, for example, used as a machine dedicated for calculating the glucose concentration $C_{gc}$, and is configured by hardware such as an application specific integrated circuit (ASIC). That is, in the concentration calculation unit 101, an algorithm for calculating the glucose concentration $C_{gc}$ based on the formula (6), the formula (10), the formula (11), and the like is configured by the hardware (hardware block).

If the measurement data $(\lambda_1:\alpha_{M1}, \lambda_2:\alpha_{M2}, \lambda_3:\alpha_{M3}, \ldots)$ and the optical path length L are input from the control unit 20, the concentration calculation unit 101 immediately calculates the glucose concentration $C_{gc}$, and outputs the calculated glucose concentration $C_{gc}$.

The optical path length L is set to be input to the data processing unit 30 from the control unit 20, along with the measurement data $(\lambda_1:\alpha_{M1}, \lambda_2:\alpha_{M2}, \lambda_3:\alpha_{M3}, \ldots)$. However, the optical path length L may be not input from the control unit 20.

For example, the optical path length L in a case where an optical path is set to cross the anterior chamber of the eye is may be set as a predetermined optical path length in the anterior chamber of the eye of a standard person. In a case where the optical path length L has a fixed value, the concentration calculation unit 101 may be included in advance.

In addition, the optical path length L may be set as an optical path length in the anterior chamber of the eye, which is measured in medical institutions and the like. In the above cases, the optical path length L may be input from the UI unit 40. The concentration calculation unit 101 may select an optical path length close to the desired optical path length among a plurality of optical path lengths which are provided in advance, from the UI unit 40.

In this manner, in a case where the optical path length L is input from the outside of the system, the data processing unit 30 may acquire the optical path length L without passing through the control unit 20.

Example 2

Figure 14:
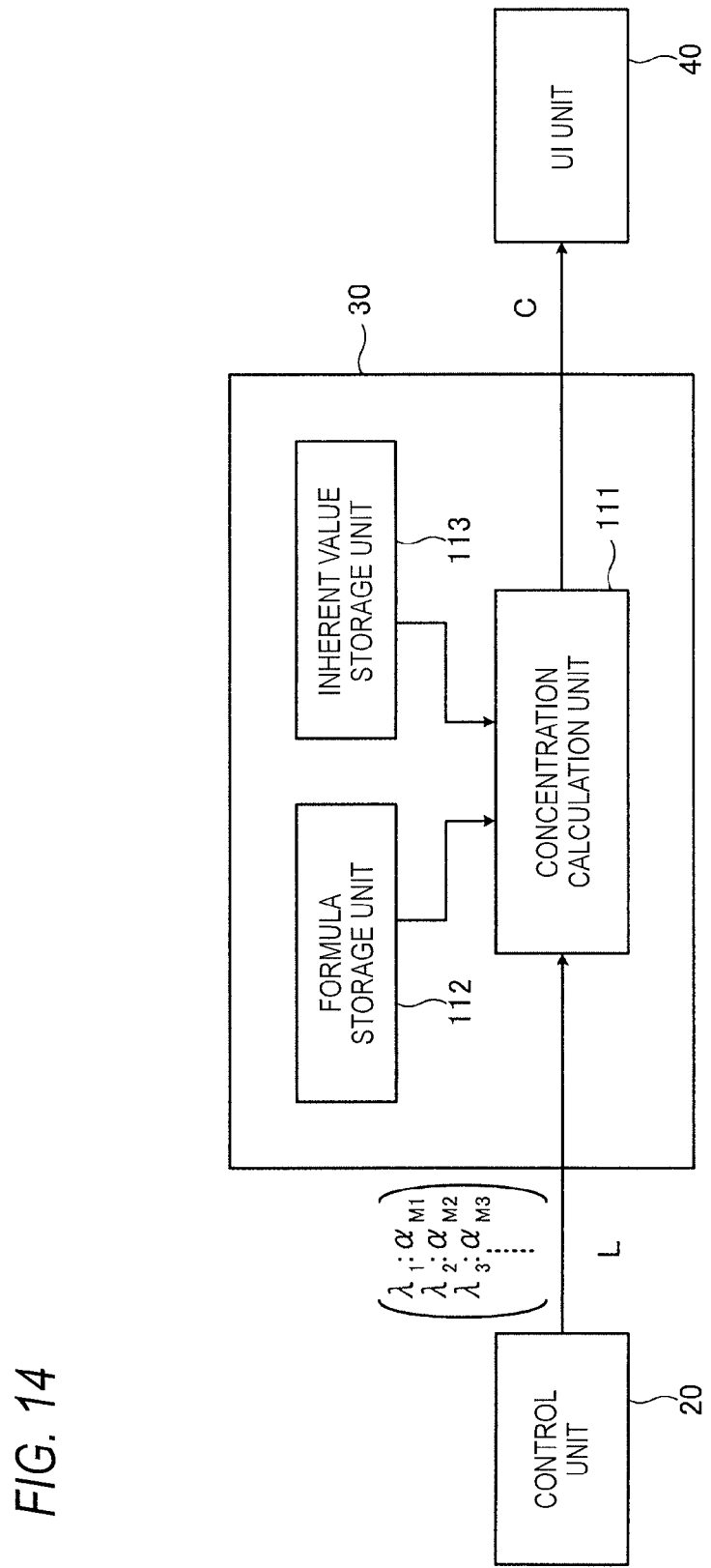
FIG. 14 is a diagram illustrating functional units of the data processing unit in Example 2.

FIG. 14 is a diagram illustrating functional units of the data processing unit 30 in Example 2.

The data processing unit 30 includes a concentration calculation unit 111, a formula storage unit 112, and an inherent value storage unit 113.

The formula storage unit 112 stores formulas (algorithms) such as the formula (6), the formula (10), and the formula (11) for calculating the concentration C of an optically active substance which is included in the measurement target 13, and is wanted to obtain the concentration. The formula storage unit 112 may store a plurality of formulas.

The inherent value storage unit 113 stores an inherent value of an optically active substance, which is obtained by being substituted with the formula for calculating the concentration C of the optically active substance. The inherent value storage unit 113 may store a plurality of inherent values which respectively correspond to a plurality of formulas.

The concentration calculation unit 111 substitutes the measurement data ($\lambda_1:\alpha_{M1}$, $\lambda_2:\alpha_{M2}$, $\lambda_3:\alpha_{M3}$, . . . ) and the optical path length L which have been transmitted from the control unit 20, and the inherent value read from the inherent value storage unit 113, for a formula read from the formula storage unit 112. The measurement data is obtained by combining the wavelength $\lambda$ and the observed optical rotation $\alpha_M$. The concentration calculation unit 111 calculates the concentration C of a predetermined optically active substance by using a result of the substitution.

The calculated concentration C of the optically active substance is displayed in a display or the like of the UI unit 40.

The optical path length L is input from the control unit 20. However, similar to Example 1, the data processing unit 30 may be included. In addition, the data processing unit 30 may acquire the optical path length L without passing through the control unit 20.

FIG. 15A and FIG. 15B are diagrams illustrating an example of a formula stored in the formula storage unit 112 and an inherent value stored in the inherent value storage unit 113. FIG. 15A illustrates an example of the formula (algorithm) stored by the formula storage unit 112. FIG. 15B illustrates examples of the inherent value stored by the inherent value storage unit 113. Here, descriptions will be made by using the aqueous humor as an example of the measurement target 13.

Firstly, the formula storage unit 112 illustrated in FIG. 15A will be described.

As an example, the formula storage unit 112 stores a plurality of formulas of #1 to #5. The formula storage unit 112 is set to store formulas, but may be a program of executing a formula. Even in this case, descriptions that the formula storage unit 112 stores formulas will be made.

As described above, a formula sets concentration in accordance with a combination of an optically active substance (first optically-active substance) wanted to be displayed in the UI unit 40, and an optically active substance (second optically-active substance) which is included in the aqueous humor other than the first optically-active substance. Thus, the formula is selected by the combination of the first optically-active substance and the second optically-active substance.

In a case of #1 where glucose is set as the first optically-active substance, and a collection of the remaining optically-active substances other than the glucose is set as the second optically-active substance, the formula (11) is selected.

In a case of #2 where albumin is set as the first optically-active substance, and a collection of the remaining optically-active substances other than the albumin is set as the second optically-active substance, the formula (12) is selected.

In a case of #3 where glucose and albumin are set as the first optically-active substances, and a collection of the remaining optically-active substances other than the glucose and the albumin is set as the second optically-active substance, the formula (6) is selected.

In a case of #4 where glucose is set as the first optically-active substance, and optically active substances which include albumin, and the remaining other than the glucose and the albumin are set as the second optically-active substances, the formula (6) is selected.

In a case of #5 where glucose is set as the first optically-active substance, and albumin is set as the second optically-active substance, the formula (10) is selected.

The formula storage unit 112 may store other combinations.

Next, the inherent value storage unit 113 illustrated in FIG. 15B will be described.

For example, the inherent value storage unit 113 stores the inherent values $A_g$ and $\lambda_g$ of glucose and the inherent value $\lambda_a$ of the albumin. Thus, a necessary inherent value is read in accordance with the formula selected from the formula storage unit 112. In addition to $\lambda_a$, $A_a$ in the formula (6) and the like may be also stored as the inherent value of the albumin.

Figure 16:
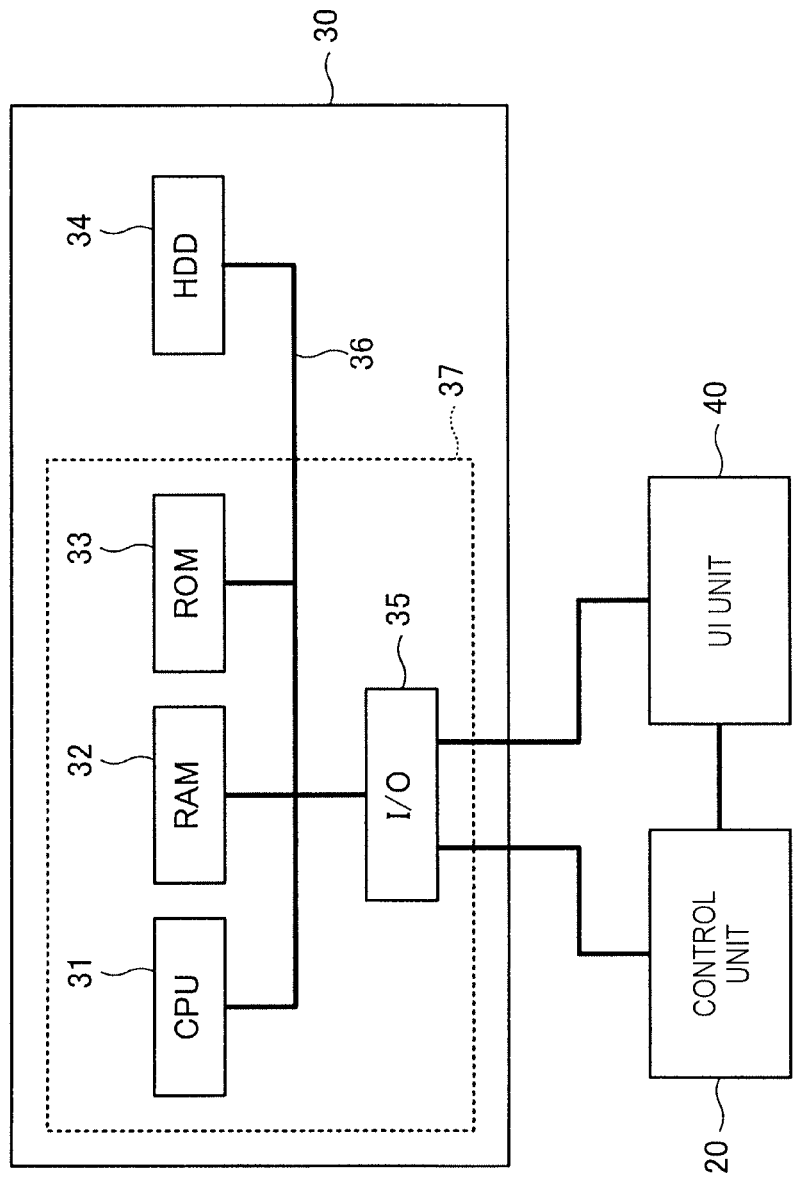
FIG. 16 is a diagram illustrating an example of a hardware configuration of the data processing unit in Example 2.

FIG. 16 is a diagram illustrating an example of a hardware configuration of the data processing unit 30 in Example 2.

The data processing unit 30 includes a central processing unit (which will be described below as a CPU) 31, a RAM 32, a ROM 33, a hard disk drive (which will be described below as a HDD) 34, an input and output interface (which will be described below as an I/O) 35.

The CPU 31, the RAM 32, the ROM 33, the HDD 34, and the I/O 35 are connected to each other through a signal bus 36.

The I/O 35 is connected to the control unit 20 and the UI unit 40 in the concentration calculation system 1 of an optically active substance.

The CPU 31, the RAM 32, the ROM 33, and the I/O 35 may be configured by using an ASIC 37 and the like.

The concentration calculation unit 111 corresponds to the CPU 31. The formula storage unit 112 and the inherent value storage unit 113 correspond to the ROM 33 or the HDD 34.

The CPU 31 includes an arithmetic logical unit (ALU) that executes a logical operation and an arithmetic operation, and the like.

The random access memory (RAM) 32 holds a program or data used in execution of an operation by the CPU 31. Generally, the RAM 32 is a volatile storage medium. The RAM 32 can read and write data and hold the written data during a period when power is supplied, and looses data if the power is not supplied.

The ROM 33 is a non-volatile storage medium (non-volatile memory). The ROM 33 can read and write data and hold the written data during a period when power is supplied, and holds the written data even when the power is not supplied. Here, the ROM 33 may be a read only memory (ROM) in which rewriting of data is not possible, and may be a flash memory in which rewriting of data is possible.

The HDD 34 is a non-volatile memory which can rewrite a large amount of data. The HDD 34 holds a program or data. The ROM 33 may hold a program or data as a firmware. In this case, the data processing unit 30 may not include the HDD 34.

If power is put into the concentration calculation system 1 of an optically active substance, the CPU 31 of the data processing unit 30 loads a program (formula) and data (inherent value) from the HDD 34 or the ROM 33 to the RAM 32.

The CPU 31 writes measurement data in the RAM 32, substitutes the loaded inherent value and the measurement data ($\lambda_1:\alpha_{M1}$, $\lambda_2:\alpha_{M2}$, $\lambda_3:\alpha_{M3}$, . . . ) for the loaded program (formula), and calculates the concentration C of an optically active substance. The measurement data is obtained by combining the wavelength λ transmitted from the control unit 20, and the observed optical rotation $\alpha_M$ measured by using the wavelength λ.

Then, the obtained concentration C of the optically active substance is displayed in a display included in the UI unit 40.

Example 3

Figure 17:
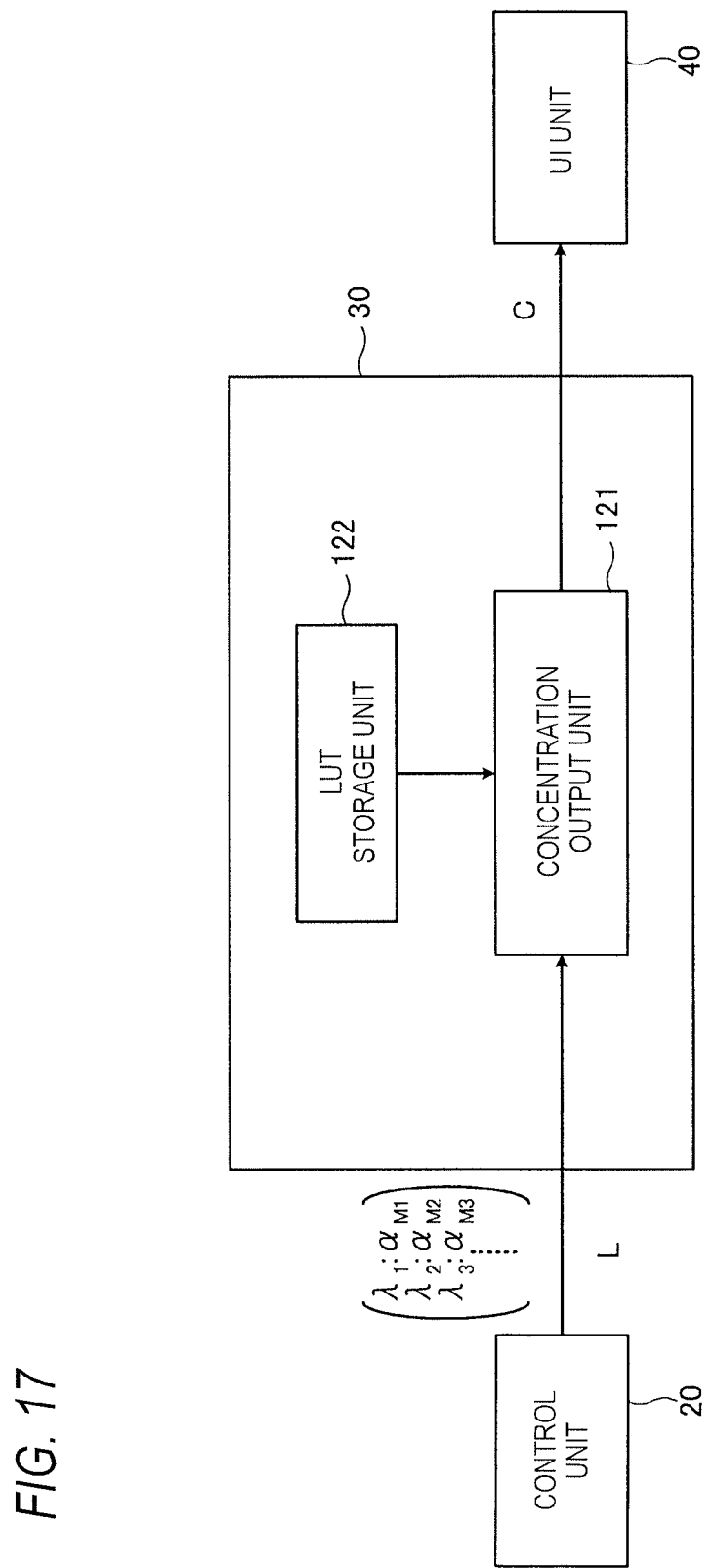
FIG. 17 is a diagram illustrating functional units of the data processing unit in Example 3.

FIG. 17 is a diagram illustrating functional units of the data processing unit 30 in Example 3.

The data processing unit 30 includes a concentration output unit 121 and a lookup-table (LUT) storage unit 122. The LUT storage unit 122 is an example of a storage unit.

The LUT storage unit 122 stores a reference table (LUT) which will be described later.

The concentration output unit 121 in the data processing unit 30 outputs the concentration C of the optically active substance, which matches a combination of the wavelength λ and the observed optical rotation $\alpha_M$, to the UI unit 40 with reference to the LUT stored by the LUT storage unit 122, based on the measurement data ($\lambda_1$:$\alpha_{M1}$, $\lambda_2$:$\alpha_{M2}$, $\lambda_3$:$\alpha_{M3}$, . . . ) obtained by combining the wavelength λ and the observed optical rotation $\alpha_M$ which are transmitted from the control unit 20.

In a case where a combination which matches with the combination of the wavelength λ and the observed optical rotation $\alpha_M$ is not in the LUT, for example, the closet combination may be selected or supplementation calculation may be performed by using a plurality of combinations.

The concentration output unit 121 may have a configuration in which the concentration C of an optically active substance, which matches with the combination of the wavelength λ and the observed optical rotation $\alpha_M$ stored by the LUT storage unit 122 is extracted. The concentration output unit 121 does not require performance for conducting an operation of calculating the concentration C of an optically active substance.

The LUT storage unit 122 may be a storage unit in which the LUT can be stored, may be a non-volatile memory such as a ROM and a HDD, and may be a non-volatile memory in which rewriting is possible.

FIG. 18 is a diagram illustrating an example of the LUT stored by the LUT storage unit 122. Here, it is assumed that the glucose concentration $C_g$ included in the aqueous humor is obtained. Three wavelengths of wavelengths $\lambda_1$, $\lambda_2$, and $\lambda_3$ are used in measurement.

As illustrated in FIG. 18, the glucose concentration $C_{gc}$ is correlated and stored in the LUT stored by the LUT storage unit 122. The glucose concentration $C_{gc}$ is calculated in advance based on the combination of the wavelength λ and the observed optical rotation $\alpha_M$ in a case where it is assumed that the measurement target 13 is irradiated with light. Thus, if the measurement data ($\lambda_1$:$\alpha_{M1}$, $\lambda_2$:$\alpha_{M2}$, and $\lambda_3$:$\alpha_{M3}$) obtained by combining the wavelength λ and the observed optical rotation $\alpha_M$ is input, the concentration output unit 121 in the data processing unit 30 acquires the glucose concentration $C_{gc}$ which matches with the combination of the measurement data ($\lambda_1$:$\alpha_{M1}$, $\lambda_2$:$\alpha_{M2}$, and $\lambda_3$:$\alpha_{M3}$) or corresponds to a close combination, with reference to the LUT of the LUT storage unit 122. The concentration output unit 121 outputs the acquired glucose concentration $C_{gc}$ to the UI unit 40. In other words, if the measurement data obtained by combining the wavelength λ and the observed optical rotation $\alpha_M$ is input, the concentration output unit 121 acquires the glucose concentration $C_{gc}$ corresponding to the input, from the LUT storage unit 122, and outputs the acquired glucose concentration $C_{gc}$ to the UI unit 40. The data stored in the LUT storage unit 122 is calculated in advance, for example, at a design step or a manufacturing step of the concentration calculation system, and is stored.

In Example 3 in which the LUT storage unit 122 is used, since the glucose concentration $C_{gc}$ which is computed in advance and is stored in the LUT storage unit 122 may be read, as in Example 1 or Example 2 in which the LUT storage unit 122 is not used, it is not necessary that the glucose concentration $C_g$ is computed and calculated based on the input measurement data ($\lambda_1$:$\alpha_{M1}$, $\lambda_2$:$\alpha_{M2}$, and $\lambda_3$:$\alpha_{M3}$). Thus, in comparison to a case where the glucose concentration $C_g$ is calculated and output based on the measurement data ($\lambda_1$:$\alpha_{M1}$, $\lambda_2$:$\alpha_{M2}$, and $\lambda_3$:$\alpha_{M3}$) which is described in Example 1 or Example 2, and is input, a period until the glucose concentration $C_g$ is output after the measurement data ($\lambda_1$:$\alpha_{M1}$, $\lambda_2$:$\alpha_{M2}$, and $\lambda_3$:$\alpha_{M3}$) is input is short.

Such a LUT can be manufactured as follows. That is, a process of acquiring a combination ($\lambda_1$:$\alpha_{M1}$, $\lambda_2$:$\alpha_{M2}$, $\lambda_3$:$\alpha_{M3}$, . . . ) of optical rotations, which respectively correspond to wavelengths of a plurality of rays is obtained; a process of calculating concentration of an optically active substance wanted to be obtained (first optically-active substance) based on a formula, and the acquired combination of the optical rotations, for each combination of the optical rotations, by using a least-squares method, the formula including a first function which represents wavelength dependence of the optical rotation in the first optically-active substance, and a second function which represents wavelength dependence of the optical rotation in other optically active substance (second optically-active substance); and a process of storing the combination of the optical rotations and concentration of the first optically-active substance which are correlated with each other, in a storage unit, the concentration of the first optically-active substance corresponding to the combination of the optical rotations are provided. In the first function, the concentration of the optically-active substance wanted to be obtained has an unknown value, and an inherent value for defining characteristics of optical rotatory dispersion of the first optically-active substance is set to a known value or an unknown value in a certain limited range. In the second function, an inherent value for defining characteristics of optical rotatory dispersion of the other optically-active substance is set to an unknown value.

In the manufacturing, not the least-squares method, but a method of solving a simultaneous equation configured by equations of which the number is the same as the number of unknown values included in a formula may be employed.

In a case where the number of wavelengths is set as m, and n pieces of observed optical rotations $\alpha_M$ for the wavelengths are set, the LUT stored by the LUT storage unit 122 stores concentrations C of m×n×n pieces of optically active substances obtained by combining (summing) the above constants.

The LUT storage unit 122 may store a plurality of LUTs.

The glucose concentration $C_{gc}$ calculated from the LUT which is stored by the LUT storage unit 122 may be provided for a fixed optical path length L such as a predetermined optical path length in the anterior chamber of the eye of a standard person. In this case, the glucose concentration $C_{gc}$ considering the optical path length L is acquired.

The glucose concentration $C_{gc}$ calculated from the LUT which is stored by the LUT storage unit 122 may be provided for a unit optical path length. In this case, the optical path length L is input from the UI unit 40 and the like, and correction for the optical path length L is performed. Since the correction for the optical path length L is simple multiplication, the concentration output unit 121 may perform the processing. The processing is performed for a short time in comparison to calculation of the glucose concentration $C_{gc}$ based on the input measurement data ($\lambda_1:\alpha_{M1}$, $\lambda_2:\alpha_{M2}$, and $\lambda_3:\alpha_{M3}$). Thus, an influence on the period until the glucose concentration $C_{gc}$ is output after the measurement data ($\lambda_1:\alpha_{M1}$, $\lambda_2:\alpha_{M2}$, and $\lambda_3:\alpha_{M3}$) is input is small.

(Display Example of Concentration C of Optically Active Substance)

In the concentration calculation system 1 of an optically active substance, a display example of the concentration C of an optically active substance to the display included in the UI unit 40 will be described. Here, an example in which the calculated glucose concentration $C_{gc}$ is displayed will be described.

Figure 19A:
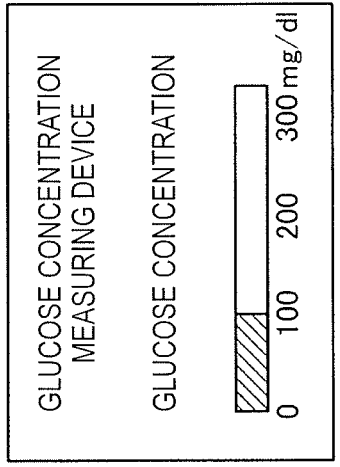
FIG. 19A is a diagram illustrating a display example of the concentration of an optically active substance with numerical values on a display included in an UI unit in a case where the concentration calculation system of an optically active substance is applied to a glucose concentration measuring device.
Figure 19B:
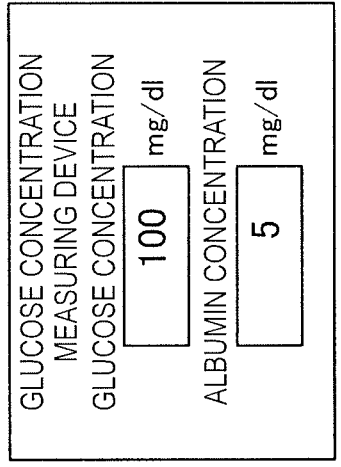
FIG. 19B is a diagram illustrating a display example of the concentration of an optically active substance with a bar graph (level) on a display included in an UI unit in a case where the concentration calculation system of an optically active substance is applied to a glucose concentration measuring device.
Figure 19C:
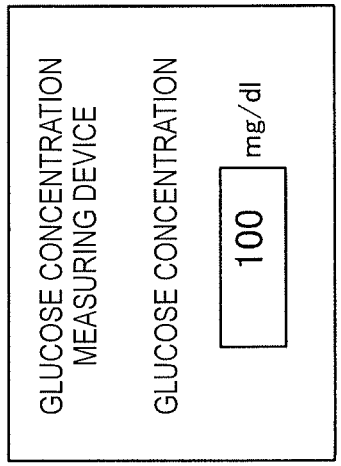
FIG. 19C is a diagram illustrating a display example of the concentration of an optically active substance with marks of "OK/NG" on a display included in an UI unit in a case where the concentration calculation system of an optically active substance is applied to a glucose concentration measuring device.
Figure 19D:
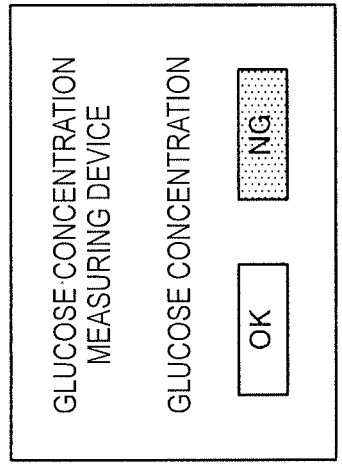
FIG. 19D is a diagram illustrating a display example of the concentration of an optically active substance in which the concentration of another optically active substance is displayed by using numerical values in addition to the glucose concentration on a display included in an UI unit in a case where the concentration calculation system of an optically active substance is applied to a glucose concentration measuring device and illustrates a display example.

FIGS. 19A-19D are diagrams illustrating display examples of concentration C of an optically active substance to a display included the UI unit 40 in a case where the concentration calculation system 1 of an optically active substance is applied to a glucose concentration measuring device. FIG. 19A illustrates a display example in which display is performed with numerical values. FIG. 19B illustrates a display example in which display is performed with a bar graph (level). FIG. 19C illustrates a display example in which display is performed with marks of "OK/NG". FIG. 19D illustrates a display example in which concentration of another optically active substance is displayed by using numerical values, in addition to the glucose concentration $C_g$.

Since FIGS. 19(*a*) and 19(*d*) are illustrated with numerical values, the change of the glucose concentration $C_{gc}$ is easily tracked. Since FIG. 19B is illustrated with a bar graph (level), the level of the glucose concentration $C_{gc}$ can be recognized at a glance. Setting as "OK" is performed in a case of being equal to or less than a predetermined threshold value, setting as "NG" is performed in a case of being more than the predetermined threshold value, and warning a user is performed in the case of "NG" in FIG. 19C. At this time, "OK" may be displayed with a green color and "NG" may be displayed with a red color.

The display examples are just an example, and may be combined. In addition, other display methods may be applied. The output of the UI unit 40 is not limited to a device displaying audiovisual information, such as a display, that is, a device such as a device giving audio information.

In a case having a purpose for measuring a blood glucose level, the glucose concentration $C_{gc}$ measured (calculated) in aqueous humor may be converted into glucose concentration in blood, and be displayed based on a correlationship between the glucose concentration in the blood and glucose concentration in the aqueous humor.

In the above descriptions, the concentration C of an optically active substance in aqueous humor, particularly, the glucose concentration $C_g$ is described.

The embodiment may be applied to a measuring device using an optical cell and the like, in addition to being applied to the aqueous humor of an eyeball of a person. An optical system in which the measurement target 13 including an optically active substance is put into the optical cell (container) and light crosses and passes through the optical cell may be provided. In this case, the optical path length L is determined by the optical cell.

The algorithm which is executed by the data processing unit 30, and is used for calculating the concentration C of an optically active substance may be used as, for example, a program executed by a general-purpose computer (PC).

For example, a user of a personal computer (PC) designates the formula, the inherent value, and the optical path length L which are used for calculating the concentration C of an optically active substance, and at least one combination and the like of the wavelengths $\lambda$ and the optical rotations $\alpha$ which are used for calculating the concentration C of an optically active substance, in a display (display screen) included in the PC. If the designation is performed, the PC executes a program and thus calculates the concentration C of an optically active substance by using the least-squares method, and displays the calculated concentration C of an optically active substance on the display (display screen). The inherent value, the optical path length L, and the combination and the like of the wavelength $\lambda$, and the optical rotation $\alpha$ which are used when the program is executed do not necessarily use the real measured results. For example, the optical rotation $\alpha$ may be acquired by actually irradiating a measurement target with light. In addition, the optical rotation $\alpha$ may be optical rotation on the assumption, that is, in a case where actually the measurement target is not irradiated with light, but irradiation with light is assumed. In this manner, the concentration is calculated under a condition set as an assumption by a user, and thus the optical rotation $\alpha$ may be used in various simulations and the like. Instead of the least-squares method, a method of solving a simultaneous equation configured by equations of which the number is the same as the number of unknown values included in a formula may be employed.

INDUSTRIAL APPLICABILITY

The concentration calculation system and the like according to the exemplary embodiment of the present invention are useful in calculating concentration of an optically active substance such as glucose or albumin, which is included in the measurement target.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A concentration calculation system of an optically active substance, the system comprising:
   a measuring unit configured to:
   irradiate a measurement target including a plurality of optically-active substances with linear polarized light of different wavelengths; and
   for each wavelength, measure an optical rotation of a polarization plane after the irradiated light passes through the measurement target; and
   a processor programmed to:
   access a formula representing optical rotation, the formula including:
   a first function representing wavelength dependence of an optical rotation of at least one first optically-active substance of the plurality of optical substances, in which: (1) a concentration of the first optically-active substance has an unknown value, and (2) at least one inherent value for defining a characteristic of optical rotatory dispersion of the first optically-active substance is a known value or an unknown value within a certain limited range; and a second function representing wavelength dependence of an optical rotation of at least one second optically-active substance of the plurality of optical substances, in which at least one inherent value for defining a characteristic of optical rotatory dispersion of the second optically-active substance is an unknown value;

calculate the concentration of the first optically-active substance based on the accessed formula and the measured optical rotations for each wavelength, by using a least-squares method; and display the calculated concentration on a display.

2. The concentration calculation system according to claim 1, wherein the at least one second optically-active substance includes a plurality of optically active substances, the second function is a function that represents wavelength dependence of optical rotations of the plurality of optically active substances as a single term, and the inherent value for defining the characteristic of optical rotatory dispersion of the plurality of optically active substances in the single term is expressed by an unknown value.

3. The concentration calculation system according to claim 1, wherein the at least one inherent value for defining characteristics of optical rotatory dispersion of the at least one first optically-active substance in the first function is at least partly an unknown value within a certain limited range.

4. The concentration calculation system according to claim 1, wherein the at least one inherent value of the at least one second optically-active substance in the second function is at least partly an unknown value within a certain limited range.

5. The concentration calculation system according to claim 1, wherein the concentration of the first optically-active substance is calculated based on the least-squares method a plurality of times while an initial value of at least one of the unknown value included in the first function and the unknown value included in the second function is changed, and when the concentration of the first optically-active substance is calculated the plurality of times, the concentration of the first optically-active substance calculated correspondingly to an initial value that causes a value of an objective function to be the greatest is not adopted as the concentration of the first optically-active substance, the objective function being expressed as a sum of squares of a difference between a theoretical value of an optical rotation obtained by using the least-squares method, and the calculated optical rotation.

6. The concentration calculation system according to claim 1, wherein the concentration of the first optically-active substance is calculated based on the least-squares method a plurality of times while at least one of a restriction condition restricting a range for the unknown value included in the first function, and a restriction condition restricting a range for the unknown value included in the second function is changed, and when the concentration of the first optically-active substance is calculated the plurality of times, the concentration of the first optically-active substance calculated correspondingly to the restriction condition of causing a value of an objective function to be the greatest is not adopted as the concentration of the first optically-active substance, the objective function being expressed as a sum of squares of a difference between a theoretical value of an optical rotation obtained by using the least-squares method, and the calculated optical rotation.

7. The concentration calculation system according to claim 1, wherein from the linearly polarized light transmitted through an aqueous humor in a person's eyeball.

8. A method of calculating a concentration of an optically active substance, the method comprising:

irradiating a measurement target including a plurality of optically-active substances with linear polarized light of different wavelengths;

for each wavelength, measuring an optical rotation of a polarization plane after the irradiated light passes through the measurement target;

accessing a formula representing optical rotation, the formula including:

a first function that represents wavelength dependence of an optical rotation in the first optically-active substance of the plurality of optical substances, in which: (1) a concentration of the first optically-active substance has an unknown value, and (2) at least one inherent value for defining a characteristic of optical rotatory dispersion of the first optically-active substance is a known value or an unknown value within a certain limited range; and a second function that represents wavelength dependence of an optical rotation in at least one second optically-active substance of the plurality of optical substances, in which at least one inherent value for defining a characteristic of optical rotatory dispersion of the second optically-active substance is an unknown value;

calculating the concentration of the first optically-active substance based on the accessed formula and the measured optical rotations for each wavelength, by using a least-squares method; and displaying the calculated concentration on a display.

9. A non-transitory computer readable medium storing a program to cause a computer to execute a function of calculating concentration of an optically active substance, the program comprising:

instructions for irradiating a measurement target including a plurality of optically-active substances with linear polarized light of different wavelengths; and instructions for measuring, for each wavelength, an optical rotation of a polarization plane after the irradiated light passes through the measurement target;

instructions for accessing a formula representing an optical rotation, the formula including:

a first function representing wavelength dependence of an optical rotation of at least one first optically-active substance of the plurality of optical substances, in which: (1) a concentration of the first optically-active substance has an unknown value, and (2) at least one inherent value for defining a characteristic of optical rotatory dispersion of the first optically-active substance is a known value or an unknown value within a certain limited range; and a second function representing wavelength dependence of an optical rotation of at least one second optically-active substance of the plurality of optical substances, in which at least one inherent value for defining a characteristic of optical rotatory dispersion of the second optically-active substance is an unknown value;

instructions for calculating the concentration of the first optically-active substance based on the accessed formula and the measured optical rotations for each wavelength, by using a least-squares method; and instructions for displaying the calculated concentration on a display.

\* \* \* \* \*